(12) United States Patent
Søe et al.

(10) Patent No.: US 6,406,723 B1
(45) Date of Patent: Jun. 18, 2002

(54) METHOD FOR PREPARING FLOUR DOUGHS AND PRODUCTS MADE FROM SUCH DOUGHS USING GLYCEROL OXIDASE AND LIPASE

(75) Inventors: Jørn Borch Søe, Mundelstrup; Charlotte Horsmans Poulsen, Bradbrand; Preben Rasmussen, Kirke Hyllinge; Susan Mampusti Madrid, Vaerløse; Masoud R. Zargahi, Århus, all of (DK)

(73) Assignee: Danisco A/S, Copenhagen (DK)

( * ) Notice: Subject to any disclaimer, the term of this patent is extended or adjusted under 35 U.S.C. 154(b) by 0 days.

(21) Appl. No.: 09/402,664

(22) PCT Filed: Apr. 3, 1998

(86) PCT No.: PCT/DK98/00136
§ 371 (c)(1),
(2), (4) Date: Oct. 22, 1999

(87) PCT Pub. No.: WO98/44804
PCT Pub. Date: Oct. 15, 1998

(30) Foreign Application Priority Data

Apr. 9, 1997 (DK) .............................................. 0400/97

(51) Int. Cl.$^7$ ................................................. A21D 8/04
(52) U.S. Cl. ........................................ 426/18; 426/554
(58) Field of Search ................................ 435/190, 198; 426/549, 18, 19, 20, 22, 24, 28, 553, 554, 653

(56) References Cited

U.S. PATENT DOCUMENTS

| 4,202,941 A | 5/1980 | Terada et al. |
| 4,399,218 A | 8/1983 | Gauhl et al. |

FOREIGN PATENT DOCUMENTS

| DE | 28 17 087 | 11/1978 |
| EP | 0 010 296 | 4/1980 |
| EP | 0 321 811 | 6/1989 |
| EP | 0 585 988 A1 | 3/1994 |
| WO | 94/04035 | 3/1994 |
| WO | 96/39851 | 12/1996 |

OTHER PUBLICATIONS

Winn et al. *Cereal Foods World*, p. 545 # 24, vol. 41(7), Jul. 1996.*
European Patent Office, Patent Abstracts of Japan, No. 06296467, dated Oct. 25, 1994.
European Patent Office, Patent Abstracts of Japan, No. 04200339, dated Jul. 21, 1992.
Abstract—XP–002077284, 12/61 (8/57 FSTA)—(C) FSTA/IFIS, 1996.
Abstract—XP–002077285 57/61 (53/57 FSTA)—(C) FSTA/IFIS, 1972.
Abstract—XP–002077286 43/61 (39/57 FSTA)—(C) FSTA/IFIS, 1979.
Abstract—XP–002077295 1/2—(C) FSTA/IFIS, 1996.
T. Uwajima et al., Agricutural and Biological Chemistry, 44 (9), pp. 2039–2045, 1980, "Properties of New Enzyme Glycerol Oxidase from *Aspergillus japonicus* AT 008.
T. Uwajima et al., Agricultural and Biological Chemistry, 43 (12), pp. 2633–2634, 1979, "Some Characteristics of a New Enzyme "Glycerol Oxidase"".
T. Uwajima et al., Methods in Enzymology, 89 (41), pp. 243–248, "Glycerol Oxidase from *Aspergillus japonicus*".
Y. Mine, Food Research International, 29 (1), 1996, pp. 81–84, "Application of the enzymatic methods to the determination of contaminated yolk in egg white".
K. Isobe et al., Journal of Molecular Catalysis B: Enzymatic 1 (1995), pp. 37–43, "A new enzymatic method for glycoladehyde production from ethylene glycol".
S. Lin et al., Enzyme and Microbial Technology 18 (1996), pp. 383–387, "Purification and characterization of a glycerol oxidase from *Penicillium* sp. TS–622".

* cited by examiner

Primary Examiner—Keith Hendricks
(74) Attorney, Agent, or Firm—Frommer Lawrence & Haug; Thomas J. Kowalski

(57) ABSTRACT

A method of improving the rheological properties of a flour dough and the quality of bread, alimentary paste products, noodles and cakes produced therefrom, wherein a combination of (a) a glycerol oxidase which does not require a co-factor to oxidize glycerol, and (b) a lipase, is added to the dough to produce a synergistic effect upon said rheological properties; and dough improving compositions containing such components.

31 Claims, 4 Drawing Sheets

BEST TRANSFORMANT

METHOD FOR PREPARING FLOUR DOUGHS AND PRODUCTS MADE FROM SUCH DOUGHS USING GLYCEROL OXIDASE AND LIPASE

This application is a 371 of PCT/DK98/00136, filed Apr. 3, 1998.

FIELD OF THE INVENTION

The present invention relates to the field of food manufacturing, in particular to the preparation of improved bakery products and other farinaceous food products. Specifically, the invention concerns the use of glycerol oxidase as a dough strengthening agent and improvement of the quality of baked and dried products made from such improved doughs. There is also provided a method of improving the properties of doughs and baked product by combined use of glycerol oxidase and a lipase.

TECHNICAL BACKGROUND AND PRIOR ART

The "strength" or "weakness" of doughs is an important aspect of making farinaceous finished products from doughs, including baking. The "strength" or "weakness" of a dough is primarily determined by its content of protein and in particular the content and the quality of the gluten protein is an important factor in that respect. Flours with a low protein content are generally characterized as "weak". Thus, the cohesive, extensible, rubbery mass which is formed by mixing water and weak flour will usually be highly extensible when subjected to stress, but it will not return to its original dimensions when the stress is removed.

Flours with a high protein content are generally characterized as "strong" flours and the mass formed by mixing such a flour and water will be less extensible than the mass formed from a weak flour, and stress which is applied during mixing will be restored without breakdown to a greater extent than is the case with a dough mass formed from a weak flour. Strong flour is generally preferred in most baking contexts because of the superior rheological and handling properties of the dough and the superior form and texture qualities of the finished baked or dried products made from the strong flour dough. Doughs made from strong flours are generally more stable. Stability of a dough is one of the most important characteristics of flour doughs. Within the bakery and milling industries it is known to use dough "conditioners" to strengthen the dough to increase its stability and strength. Such dough conditioners are normally non-specific oxidizing agents such as e.g. iodates, peroxides, ascorbic acid, K-bromate or azodicarbonamide and they are added to dough with the aims of improving the baking performance of flour to achieve a dough with improved stretchability and thus having a desirable strength and stability. The mechanism behind this effect of oxidizing agents is that the flour proteins, in particular gluten contains thiol groups which, when they become oxidized, form disulphide bonds whereby the protein forms a more stable matrix resulting in a better dough quality and improvements of the volume and crumb structure of the baked products.

However, the use of several of the currently available non-specific oxidizing agents is either objected to by consumers or is not permitted by regulatory bodies. Hence it has been attempted to find alternatives to these conventional flour and dough additives, and the prior art has i.a. suggested the use of glucose oxidase and hexose oxidase for this purpose.

Glycerol oxidase is an oxidoreductase which is capable of oxidizing glycerol. Different types of glycerol oxidase have been described in the literature. Some of these glycerol oxidases need co-factors in order to oxidize glycerol (Shuen-Fu et al., 1996. Enzyme Micro. Technol., 18:383–387).

However, glycerol oxidase from *Aspergillus japonicus* does not require any co-factors in the oxidation of glycerol to glyceraldehyd (T. Uwajima and O. Terada, 1980. Agri. Biol. Chem. 44:2039–2045).

This glycerol oxidase has been characterized by T. Uwajima and O. Terada (Methods in Enzymology, 1982, 89:243–248) and T. Uwajima et al. (Agric. Biol. Chem., 1979, 43:2633–2634), and has a pH optimum at 7.0 and $K_m$ and $V_{max}$ are 10.4 mM and 935.6 $\mu$mol $H_2O_2$ min$^{-1}$ respectively using glycerol as substrate. The enzyme is most active on glycerol but also other substrates like dihydroxyacetone, 1,3-propanediol, D-galactose ad D-fructose are oxidized by glycerol oxidase.

Glycerol oxidase not requiring co-factors has also been isolated from Penicillium and characterized by Shuen-Fuh Lin et al. (Enzyme Micro. Technol., 1996, 18:383–387). This enzyme has optimum activity in the pH range from 5.5 to 6.5 at 30° C. The enzyme is stable between 20 and 40° C. but loses its activity at temperatures above 50° C.

Other potential sources for glycerol oxidase according to the invention include different fungal species as disclosed in DE-2817087-A, such as *Aspergillus oryzae, Aspergillus parasiticus, Aspergillus flavus, Neurospora crassa, Neurospora sitophila, Neurospora tetrasperma, Penicillium nigricans, Penicillium funiculosum* and *Penicillium janthinellum*.

Glycerol oxidase isolated from the above natural sources has been used for different applications. Thus, glycerol oxidase from *Aspergillus japonicus* has been used for glycoaldehyde production from ethylene glycol (Kimiyasu Isobe and Hiroshi Nishise, 1995, Journal of Molecular Catalysis B: Enzymatic, 1:37–43). Glycerol oxidase has also been used in the combination with lipoprotein lipase for the determination of contaminated yolk in egg white (Yioshinori Mie, 1996. Food Research International, 29:81–84). DE-2817087-A and U.S. Pat. No. 4,399,218 disclose the use of glycerol oxidase for the determination of glycerol.

It has now been found that the addition of a glycerol oxidase to a flour dough results in an increased resistance hereof to deformation when the dough is stretched, i.e. this enzyme confers to the dough an increased strength whereby the dough becomes less prone to mechanical deformation. Accordingly, glycerol oxidase is highly useful as a dough conditioning agent in the manufacturing of flour dough based products including not only bread products but also other products made from flour doughs such as noodles and alimentary paste products.

It has also been found that the dough strengthening effect of glycerol oxidase is potentiated significantly when it is combined with a lipase, which in itself does not affect the dough strength. Furthermore, the combined use of glycerol oxidase and lipase results in an improvement of bread quality, in particular in respect of specific volume and crumb homogeneity, which is not a simple additive effect, but reflects a synergistic effect of these two types of enzymes.

SUMMARY OF THE INVENTION

Accordingly, the invention relates in a first aspect to a method of improving the rheological properties of a flour dough and the quality of the finished product made from the dough, comprising adding to the dough 10 to 10,000 units of a glycerol oxidase per kg of flour.

In a further aspect there is provided a method of improving the rheological properties of a flour dough and the quality of the finished product made from the dough, comprising adding to the dough a glycerol oxidase and a lipase.

The invention pertains in a still further aspect to dough improving composition comprising a glycerol oxidase and at least one further dough ingredient or dough additive.

In still further aspects, the invention relates to the use of a glycerol oxidase for improving the rheological properties of a flour dough and the quality of the finished product made from the dough and to the use of a glycerol oxidase and a lipase in combination for improving the rheological properties of a flour dough and the quality of the finished product made from the dough.

DETAILED DISCLOSURE OF THE INVENTION

In one aspect, the present method provides a method of improving the rheological properties of flour doughs.

The expression "rheological properties" as used herein refers particularly to the effects of dough conditioners on dough strength and stability as the most important characteristics of flour doughs. According to American Association of Cereal Chemists (AACC) Method 36-01A the term "stability" can be defined as "the range of dough time over which a positive response is obtained and that property of a rounded dough by which it resists flattening under its own weight over a course of time". According to the same method, the term "response" is defined as "the reaction of dough to a known and specific stimulus, substance or set of conditions, usually determined by baking it in comparison with a control"

As it is mentioned above, it is generally desirable to improve the baking performance of flour to achieve a dough with improved stretchability and thus having a desirable strength and stability by adding oxidizing agents which cause the formation of protein disulphide bonds whereby the protein forms a more stable matrix resulting in a better dough quality and improvements of the volume and crumb structure of baked products.

Thus, the term "rheological properties" relates to the above physical and chemical phenomena which in combination will determine the performance of flour doughs and thereby also the quality of the resulting products.

The method comprises, as it is mentioned above, the addition of an effective amount of a glycerol oxidase to the dough. It will be understood that the addition can be either to a component of the dough recipe or to the dough resulting from mixing all of the components for the dough. In the present context, "an effective amount" is used to indicate that the amount is sufficient to confer to the dough and/or the finished product improved characteristics as defined herein. Specifically, such an amount is in the range of 10 to 10,000 units of glycerol oxidase per kg flour.

In one useful embodiment of the method according to the invention, the glycerol oxidase can, as it is described in details herein, be isolated from a bacterial species, a fungal species, a yeast species, an animal cell including a human cell or a plant cell. Examples of glycerol oxidase producing fungal species are species belonging to the genera Aspergillus, Neurospora and Penicillium, such as *A. japonicus, A. oryzae, A. parasiticus, A. flavus, Neurospora crassa, N. sitophila, N. tetrasperma, Penicillium nigricans, P. funiculosum* and *P. janthinellum.*

Glycerol oxidase can be derived as a native enzyme from natural sources such as the above.

It is one objective of the invention to provide improved bakery products. In accordance with the invention, a bakery product dough including a bread dough is prepared by mixing flour with water, a leavening agent such as yeast or a conventional chemical leavening agent, and an effective amount of glycerol oxidase under dough forming conditions. It is, however, within the scope of the invention that further components can be added to the dough mixture.

Typically, such further dough components include conventionally used dough components such as salt, sweetening agents such as sugars, syrups or artificial sweetening agents, lipid substances including shortening, margarine, butter or an animal or vegetable oil, glycerol and one or more dough additives such as emulsifying agents, starch degrading enzymes, cellulose or hemicellulose degrading enzymes, proteases, lipases, non-specific oxidizing agents such as those mentioned above, flavouring agents, lactic acid bacterial cultures, vitamins, minerals, hydrocolloids such as alginates, carrageenans, pectins, vegetable gums including e.g. guar gum and locust bean gum, and dietary fiber substances.

Conventional emulsifying agents used in making flour dough products include as examples monoglycerides, diacetyl tartaric acid esters of mono- and diglycerides of fatty acids, and lecithins e.g. obtained from soya. Among starch degrading enzymes, amylases are particularly useful as dough improving additives. Other useful starch degrading enzymes which may be added to a dough composition include glucoamylases and pullulanases. In the present context, further interesting enzymes are xylanases and oxidoreductases such as glucose oxidase, pyranose oxidase, hexose oxidase, sulfhydryl oxidase, and lipases.

A preferred flour is wheat flour, but doughs comprising flour derived from other cereal species such as from rice, maize, barley, rye and durra are also contemplated.

In accordance with the invention, the dough is prepared by admixing flour, water, the glycerol oxidase and optionally other ingredients and additives. The glycerol oxidase can be added together with any dough ingredient including the water or dough ingredient mixture or with any additive or additive mixture. The dough can be prepared by any conventional dough preparation method common in the baking industry or in any other industry making flour dough based products.

The glycerol oxidase can be added as a liquid preparation or in the form of a dry powder composition either comprising the enzyme as the sole active component or in admixture with one or more other dough ingredients or additive.

The amount of the glycerol oxidase added is an amount which results in the presence in the dough of 10 to 5,000 units (as defined in the following) such as 10 to 2,500 units per kg of flour. In useful embodiments, the amount is in the range of 20 to 1,500 units per kg of flour.

The effect of the glycerol oxidase on the Theological properties of the dough can be measured by standard methods according to the International Association of Cereal Chemistry (ICC) and the American Association of Cereal Chemistry (AACC) including the amylograph method (ICC 126), the farinograph method (AACC 54-21) and the extensigraph method (AACC 54-10). The AACC method 54-10 defines the extensigraph in the following manner: "the extensigraph records a load-extension curve for a test piece of dough until it breaks. Characteristics of load-extension curves or extensigrams are used to assess general quality of flour and its responses to improving agents". In effect, the extensigraph method measures the relative strength of a dough. A strong dough exhibits a higher and, in some cases, a longer extensigraph curve than does a weak dough.

In a preferred embodiment of the method according to the invention, the resistance to extension of the dough in terms of the ratio between the resistance to extension (height of curve, B) and the extensibility (length of curve, C), i.e. the B/C ratio as measured by the AACC method 54-10 is increased by at least 10% relative to that of an otherwise similar dough not containing glycerol oxidase. In more preferred embodiments, the resistance to extension is increased by at least 20%, such as at least 50% and in particular by at least 100%.

It has been found that the addition of glycerol oxidase to bakery product doughs results in bakery products such as yeast leavened and chemically leavened products in which the specific volume is increased relative to an otherwise similar bakery product, prepared from a dough not containing glycerol oxidase. In this context, the expression "specific volume" is used to indicate the ratio between volume and weight of the product. It has been found that, in accordance with the above method, the specific volume can be increased significantly such as by at least 10%, preferably by at least 20%, including by at least 30%, preferably by at least 40% and more preferably by at least 50%.

The method according to the invention is highly suitable for improving the rheological properties and quality of the finished products of conventional types of yeast leavened bread products based on wheat flour, such as loaves and rolls. The method is also suitable for improving the rheological properties of doughs containing chemical leavening agents (baking powder) and the quality of products made from such doughs. Such product include as examples sponge cakes and muffins.

In one interesting aspect, the invention is used to improve the Theological properties of doughs intended for noodle products including "white noodles" and "chinese noodles" and to improve the textural qualities of the finished noodle products. A typical basic recipe for the manufacturing of noodles comprises the following ingredients: wheat flour 100 parts, salt 0.5 parts and water 33 parts. Furthermore, glycerol is often added to the noodle dough. The noodles are typically prepared by mixing the ingredients in an appropriate mixing apparatus followed by rolling out the noodle dough using an appropriate noodle machine to form the noodle strings which are subsequently air dried.

The quality of the finished noodles is assessed i.a. by their colour, cooking quality and texture. The noodles should cook as quickly as possible, remain firm after cooking and should preferably not loose any solids to the cooking water. On serving the noodles should preferably have a smooth and firm surface not showing stickiness and provide a firm "bite" and a good mouthfeel. Furthermore, it is important that the white noodles have a light colour.

Since the appropriateness of wheat flour for providing noodles having the desired textural and eating qualities may vary according to the year and the growth area, it is usual to add noodle improvers to the dough in order to compensate for sub-optimal quality of the flour. Typically, such improvers will comprise dietary fiber substances, vegetable proteins, emulsifiers and hydrocolloids such as e.g. alginates, carrageenans, pectins, vegetable gums including guar gum and locust bean gum, and amylases, and as mentioned above, glycerol.

It is therefore an important aspect of the invention that the glycerol oxidase according to the invention is useful as a noodle improving agent optionally in combination with glycerol and other components currently used to improve the quality of noodles. Thus, it is contemplated that noodles prepared in accordance with the above method will have improved properties with respect to colour, cooking and eating qualities including a firm, elastic and non-sticky texture and consistency.

In a further useful embodiment, the dough which is prepared by the method according to the invention is a dough for preparing an alimentary paste product. Such products which include as examples spaghetti and maccaroni are typically prepared from a dough comprising main ingredients such as flour, eggs or egg powder and/or water. After mixing of the ingredient, the dough is formed to the desired type of paste product and air dried. It is contemplated that the addition of glycerol oxidase to a paste dough, optionally in combination with glycerol, will have a significant improving effect on the extensibility and stability hereof resulting in finished paste product having improved textural and eating qualities.

In a useful embodiment, there is provided a dough improving method wherein at least one further enzyme is added to the dough ingredient, dough additive or the dough. In the present context, suitable enzymes include cellulases, hemicellulases, xylanases, starch degrading enzymes, oxidoreductases and proteases.

In a further aspect, the invention relates to a method of improving the rheological properties of a flour dough and the quality of the finished products made from the dough which comprises that both a glycerol oxidase and a lipase is added to the dough.

It was surprisingly found that the two types of enzymes were capable of interacting with each other under the dough conditions to an extent where the effect on improvement of the dough strength and bread quality by the enzymes was not only additive, but the effect was synergistic.

Thus, with respect to improvement of dough strength it was found that with glycerol oxidase alone, the B/C ratio as measured after 45 minutes of resting was increased by 34%, with lipase alone no effect was observed. However, when combining the two enzymes, the B/C ratio was increased by 54%, i.e. combining the glycerol oxidase with the lipase enhanced the dough strengthening effect of glycerol oxidase by more than 50%. Thus, one objective of combining glycerol oxidase and a lipase is to provide an enhancement of the dough strengthening effect of glycerol oxidase by at least 25% such as at least 50% including at least 75%, determined as described herein.

In relation to improvement of finished product, it was found that the combined addition of glycerol oxidase and a lipase resulted in a substantial synergistic effect in respect to crumb homogeneity as defined herein. Also, with respect to the specific volume of baked product a synergistic effect was found. Thus, for a bread product, the addition of lipase alone typically results in a negligible increase of the specific volume, addition of glycerol oxidase alone in an increase of about 25%, whereas a combined addition of the two enzymes results in an increase of more than 30%.

Further in relation to improvement of the finished product, it was found that the addition of lipase resulted in modification of the glycolipids, monogalactosyl diglyceride and digalactosyl diglyceride present in dough. These components were converted to the more polar components monogalactosyl monoglyceride and digalactosyl monoglyceride. As galactosyl monoglycerides are more surface active components than galactosyl diglycerides it is assumed that galactosyl monoglycerides contributed to the observed improved crumb cell structure and homogeneity. Thus, one objective of using lipase is to hydolyse at least 10% of the galactosyl diglycerides normally present in a flour dough to the corresponding galactosyl monoglycerides, such as at least 50% including at least 100%.

The details of such a method using combined addition of glycerol oxidase and lipase are, apart from the use of a lipase in combination with glycerol oxidase, substantially similar to those described above for a method according to the invention which does not require the addition of a lipase.

When using, in accordance with the invention, a lipase in combination with a glycerol oxidase, the amount of lipase is typically in the range of 10 to 100,000 lipase units (LUS) (as defined in the following) per kg flour including the range of 10 to 20,000 LUS, e.g. 100 to 15,000 LUS such as 500 to 10,000 LUS.

Lipases that are useful in the present invention can be derived from a bacterial species, a fungal species, a yeast species, an animal cell and a plant cell. Whereas the enzyme may be provided by cultivating cultures of such source organisms naturally producing lipase, it may be more convenient and cost-effective to produce it by means of genetically modified cells such as it is described in details in the following examples. In the latter case, the term "derived" may imply that a gene coding for the lipase is isolated from a source organism and inserted into a host cell capable of expressing the gene.

Thus, the enzyme may in a useful embodiment be derived from an Aspergillus species including as examples *A. tubigensis, A. oryzae* and *A. niger*.

Presently preferred lipases include the lipase designated Lipase 3, the production and characteristics of which is described in details in the following examples, or a mutant of this enzyme. In the present context, the term "mutant" refers to a lipase having, relative to the wild-type enzyme, an altered amino acid sequence. A further preferred lipase is the lipase found in the commercial product, GRINDAMYL™ EXEL 16.

In a further aspect of the invention there is provided a dough improving composition comprising a glycerol oxidase and at least one further dough ingredient or dough additive.

The further ingredient or additive can be any of the ingredients or additives which are described above. The composition may conveniently be a liquid preparation comprising the glycerol oxidase. However, the composition is conveniently in the form of a dry composition.

The amount of the glycerol oxidase in the composition is in the range of 10 to 10,000 units per kg flour. It will be appreciated that this indication of the amount of enzyme implies that a recommended appropriate amount of the composition will result in the above stated amount in the dough to which it is added. In specific embodiments, the amount of glycerol oxidase is in the range of 10 to 5,000 units such as 10 to 2,500 units per kg of flour. In other useful embodiments, the amount is in the range of 20 to 1,500 units per kg of flour.

In another embodiment, the dough improving composition may further comprises a lipase as defined above and in the amounts as also described above in relation to the method according to the invention.

Optionally, the composition is in the form of a complete dough additive mixture or pre-mixture for making a particular finished product and containing all of the dry ingredients and additives for such a dough. In specific embodiments, the composition is one particularly useful for preparing a baking product or in the making of a noodle product or an alimentary paste product.

In one advantageous embodiment of the above method at least one further enzyme is added to the dough. Suitable examples hereof include a cellulase, a hemicellulase, a xylanase, a starch degrading enzyme, hexose oxidase and a protease.

In a preferred advantageous embodiment, the further added enzyme is a lipase. It has been found that in accordance with the above method, the crumb homogeneity and specific volume of the bakery product can be increased significantly as compared to that of an otherwise similar bakery product prepared from a dough not containing glycerol oxidase, and from a similar bakery product prepared from a dough containing glycerol oxidase.

In a still further aspect, the present invention pertains to the use of a glycerol oxidase and a lipase in combination for improving the rheological properties of a flour dough and the quality of the finished product made from the dough.

In this connection, specific embodiments include use wherein the improvement of the rheological properties of the dough include that the resistance to extension of the dough in terms of the ratio between resistance to extension (height of curve, B) and the extensibility (length of curve, C), i.e. the B/C ratio, as measured by the AACC method 54-10 is increased by at least 10% relative to that of an otherwise similar dough that does not contain glycerol oxidase and use wherein the improvement of the quality of the finished product made from the dough is that the average pore diameter of the crumb of the bread made from the dough is reduced by at least 10%, relative to a bread which is made from a bread dough without addition of the lipase.

In a further embodiment, the use according to the invention, implies that the improvement of the quality of the finished product made from the dough consists in that the pore homogeneity of the crumb of the bread made from the dough is incresed by at least 5%, relative to a bread which is made from a bread dough without addition of the lipase. The pore homogeneity of bread is conveniently measured by means of an image analyzer composed of a standard CCD-video camera, a video digitiser and a personal computer with WinGrain software. Using such an analyzer, the results of pore diameter in mm and pore homogeneity can be calculated as an average of measurements from 10 slices of bread. The pore homogeneity is expressed in % of pores that are larger than 0.5 times the average of pore diameter and smaller than 2 times the average diameter.

In a further embodiment, the use relates to improvement of the rheological characteristics of the dough including that the gluten index (as defined hereinbelow) in the dough is increased by at least 5%, relative to a dough without addition of a lipase, the gluten index is determined by means of a Glutomatic 2200 apparatus.

BRIEF DESCRIPTION OF THE FIGURES

The present invention is further illustrated by reference to the accompanying figures in which.

Figure 1:
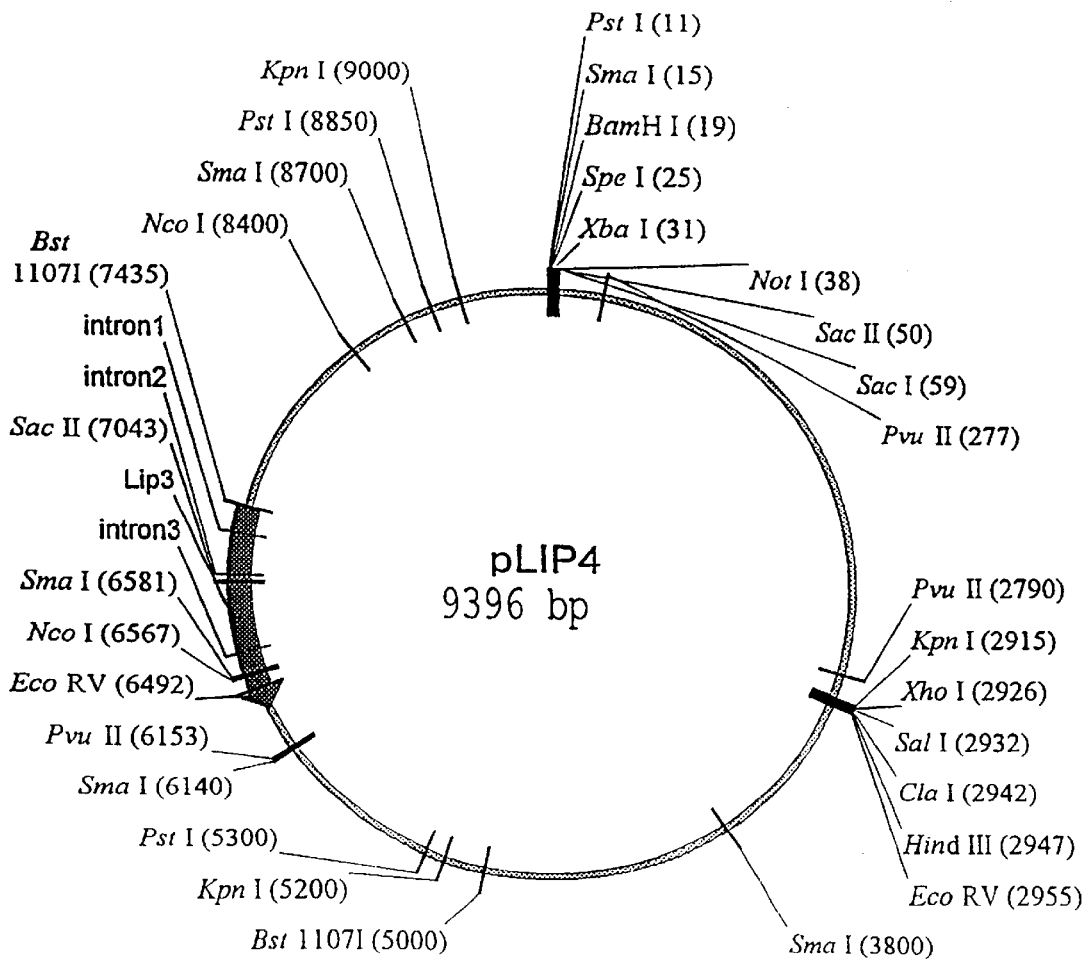
FIG. 1 shows the restriction map of the genomic clone of the lipA gene.
Figure 2:
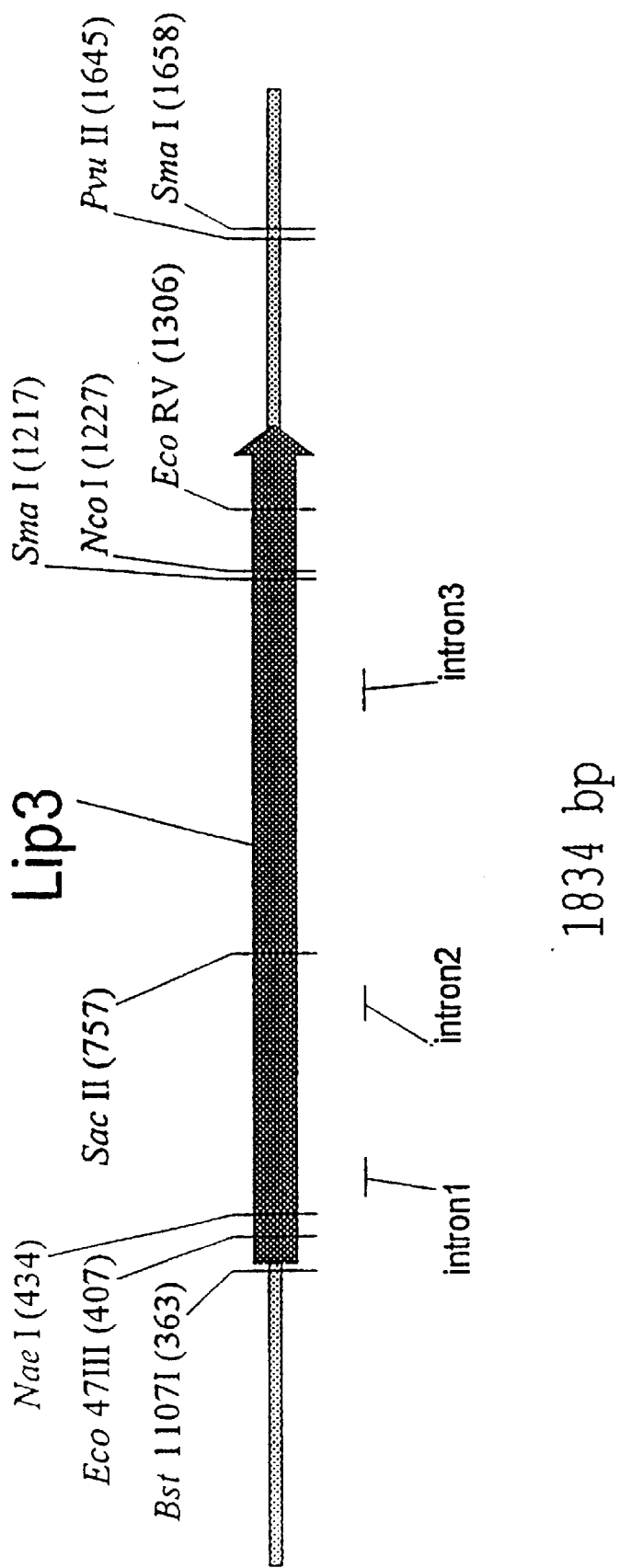
FIG. 2 shows the structure of the lipA gene encoding lipase 3.

The invention will now be described by way of illustration in the following non-limiting examples.

A. PRODUCTION AND PURIFICATION OF GLYCEROL OXIDASE (GLOX)

EXAMPLE 1

Production, extraction and purification of glycerol oxidase using different strains and cultivation conditions 1. Production, extraction and purification of glycerol oxidase using *Aspergillus japonicus* ATCC 1042 cultivated in a production medium containing 3% glycerol The following assay for determination of glycerol oxidase activity was used:

The assay is based on the method described by Sullivan and Ikawa (Biochimica and Biophysica Acta, 1973, 309:11–22), but modified as described in the following. An assay mixture containing 150 μl 2% glycerol (in 100 mM phophate buffer, pH 7.0), 120 μl 100 mM phosphate buffer, pH 7.0, 10 μl o-dianisidin dihydrochloride (Sigma D 3252, 3 mg/ml in H$_2$O), 10 μl peroxidase (POD) (Sigma P8125, 0.1 mg/ml in 100 mM phosphate buffer, pH 7.0) and 10 μl glycerol oxidase (GLOX) solution. The controls are made by adding buffer in place of GLOX solution. The incubation is started by the addition of glycerol. After 15 minutes of incubation at 25° C. in microtiter plates, the absorbance at 402 nm is read in a Elisa reader. A standard curve is constructed using varying concentrations of H$_2$O$_2$ in place of the enzyme solution. The reaction can be described in the following manner:

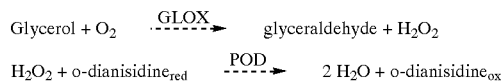

Oxidised o-dianisidine has a yellow colour absorbing at 402 nm.

One glycerol oxidase unit (U) is the amount of enzyme which catalyses the production of 1 μmole H$_2$O$_2$ per minute at 25° C., pH 7.0 at a substrate concentration of 0.2 M glycerol.

A spore suspension of *Aspergillus japonicus* ATCC 1042 was prepared by incubating *A. japonicus* on PDA medium (30° C., 7 days) and washing with 10 ml of 0.2% Tween 80. A preculture was prepared by inoculating 1 ml of the resulting spore suspension in 300 ml production medium containing 3.0% of glycerol (87%, Merck), 0.3% of yeast extract (Difco), 0.1% of meat extract (Difco), 0.1% KH$_2$PO$_4$ (Merck), 0.1% of MGSO$_4$*7H$_2$O (Merck), 0.1% antifoam (Contra spum) and 70 mg/l of chloramphenicolum (Mecobenzon) (pH adjusted to 7.2 with NaOH) in a 500 ml flask. The preculture was incubated overnight at 30° C. with shaking (200 rpm).

A 30 liter fermenter with 15 liter production medium was inoculated with 900 ml (corresponding to 3 flasks) of the resulting overnight preculture, and cultured at 30° C. for 25 hours under continuous stirring (350 rpm) and aeration (15 l/min). After culturing, the mycelia was harvested from the resulting culture broth by filtration on a Whatman GF/B filter by suction, and washed with 3 liters of deionized water. The mycelium yield was 186 g (wet weight).

A part (50 g) of the resulting mycelial mat was suspended in 700 ml of 50 mM borate buffer (pH 10.0), and disrupted by ultrasonication (Branson, Sonifer 250) at 5° C. (3×5 minutes). After disruption, the mycelia was removed by centrifugation (29,000 g for 15 minutes), the cell-free extract (700 ml) was brought to 40% saturation with ammonium sulfate and the resulting precipitate was removed by centrifugation (29,000 g for 20 minutes). The ammonium sulfate concentration was then increased to 70% saturation to precipitate the enzyme. The resulting precipitate was collected and solubilized in 100 ml of 50 mM borate buffer (pH 10.0). The crude extract was then dialysed for 24 hours against 5 l of 50 mM borate buffer (pH 10.0). After dialysis the insoluble matters in the crude extract were removed by centrifugation (18,000×g for 10 minutes). The resulting supernatant contained 8.7 units of glycerol oxidase activity per ml.

2. Production extraction and purification of glycerol oxidase using *Aspergillus japonicus* ATCC 1042 cultivated in a production medium containing 5% glycerol A spore suspension of *Aspergillus japonicus* ATCC 1042 was prepared as described above. A preculture was prepared by inoculating 1 ml of the resulting spore suspension into a flask (500 ml) containing 200 ml production medium (5.0% glycerol, 0.25% yeast extract, 0.1% Malt extract, 0.7% antifoam (Contra spum), pH adjusted to 6.2 with HCl, sterilization at 121° C. for 90 minutes). The preculture was incubated 3 days at 30° C. with continuous shaking (200 rpm). A 6 liter fermenter with 5 liter production medium as described above was inoculated with 50 ml of the resulting preculture and cultured at 30° C. for 3 days under continuous stirring (250 rpm) and aeration (5 l/min). After culturing the mycelia was harvested from the resulting culture broth by filtration on a Whatman GF/B filter by suction, and washed with 3 liter ionized water containing 0.9% NaCl. The resulting mycelia mat was frozen in liquid nitrogen, suspended in 200 ml of 50 mM phosphate buffer (pH 7.0) and disrupted by ultrasonication (Branson, Sonifer 250) at 5° C. (4 minutes). After disruption, the mycelia was removed by filtration on a Whatman GF/A filter by suction. The enzyme in the resulting filtrate was concentrated on a AMICON® 8400 ultrafiltration unit and contained 87 units of glycerol oxidase per ml after ultrafiltration.

3. Production, extraction and purification of glycerol oxidase using *Aspergillus japonicus* ATCC 1042 cultivated in a production medium containing 10% glycerol A spore suspension of *Aspergillus japonicus* ATCC 1042 was prepared as described above. A 1 ml sample of the resulting spore suspension was inoculated into each of 5 flasks (500 ml) with 200 ml production medium containing 10.0% of glycerol, 0.1% of yeast extract and 0.1% of malt extract (pH adjusted to 6.2 with HCl, sterilization at 121° C. for 15 minutes). The cultures were incubated for 5 days at 30° C. with shaking (140 rpm).

The extraction and concentration of the enzyme was carried out as described above. The resulting filtrate contained 66 units of glycerol oxidase per ml after ultrafiltration.

4. Production of glycerol oxidase from *Penicillium funiculosum* and *Penicillium janthinellum*

Spore suspensions of *Penicillium funiculosum* NRRL 1132 and *Penicillium janthinellum* NRRL 2016 were prepared as described above. A 1 ml sample of each of the resulting spore suspensions was inoculated into separate flasks (1000 ml) containing 100 g wheat bran and 100 ml water (two flasks for each culture)

Glycerol oxidase was extracted by suspending the wheat bran cultures in 900 ml of 30 mM phosphate buffer (pH 6.5) containing 0.1% Triton X100 (Merck). The mycelial mat was removed from the cultivation media by filtration using a Whatman GF/B filter. The resulting mycelia mat was frozen in liquid nitrogen, suspended in 200 ml of 50 mM phosphate buffer (pH 7.0) and disrupted by ultrasonication (Branson, Sonifer 250) at 5° C. (4 minutes). After disruption, the mycelia was removed by filtration on a Whatman GF/A filter by suction. The resulting filtrate from the *Penicillium funiculosum* culture contained 7.4 units of glycerol oxidase per ml, and the resulting filtrate from the *Penicillium janthinellum* culture contained 11.3 units of glycerol oxidase per ml.

B. PRODUCTION, PURIFICATION AND CHARACTERIZATION OF *Aspergillus tubigensis* LIPASE 3

MATERIALS AND METHODS (i) Determination of lipase activity and protein

1. Plate assay on tributyrin-containing medium

The assay is modified from Kouker and Jaeger (Appl. Environ. Microbiol., 1987, 53:211–213).

A typical protocol for this assay is as follows: 100 ml 2% agar in 50 mM sodium phosphate buffer (pH 6.3) is heated to boiling, and after cooling to about 70° C. under stirring, 5 ml 0.2% Rhodamine B is added under stirring plus 40 ml of tributyrin. The stirring is continued for 2 minutes. The mixture is then sonicated for 1 minute. After an additional 2 minutes of stirring, 20 ml of the agar mixture is poured into individual petri dishes. In the absence of lipase activity, the agar plates containing tributyrin and Rhodamine B will appear opaque and are pink coloured.

To quantify lipase activity, holes having a diameter of 3 mm are punched in the above agar and filled with 10 $\mu$l of lipase preparation. The plates are incubated for varying times at 37° C. When lipase activity is present in the applied preparation to be tested, a sharp pink/reddish zone is formed around the holes. When the plates are irradiated with UV light at 350 nm, the lipase activity is observed as halos of orange coloured fluorescence.

2. Modified Food Chemical Codex assay for lipase activity

Lipase activity based on hydrolysis of tributyrin is measured according to Food Chemical Codex, Forth Edition, National Academy Press, 1996, p. 803. With the modification that the pH is 5.5 instead of 7. One LUT (lipase unit tributyrin) is defined as the amount of enzyme which can release 2 $\mu$mol butyric acid per min. under the above assay conditions.

3. p-nitrophenyl acetate assay

Lipase activity can also be determined colorimetrically using p-nitrophenyl acetate as a substrate e.g. using the following protocol: In a microtiter plate 10 $\mu$l of sample or blank is added followed by the addition of 250 $\mu$l substrate (0.5 mg p-nitrophenyl acetate per ml 50 mM phosphate buffer, pH 6.0). The microtiter plate is incubated for 5 minutes at 30° C. and the absorbance at 405 nm is read using a microplate reader. 1 unit is defined as 1 $\mu$mol p-nitrophenol released per 5 minutes.

4. p-nitrophenyl hexanoate assay

Lipase activity can be determined by using p-nitrophenyl hexanoate as a substrate. This assay is carried out by adding 10 $\mu$l of sample preparation or blank to a microtiter plate followed by the addition of 250 $\mu$l substrate (0.5 mg p-nitrophenyl hexanoate per ml of 20 mM phosphate buffer, pH 6.). At this concentration of substrate the reaction mixture appears as a milky solution. The microtiter plate is incubated for 5 minutes at 30° C. and the absorbance at 405 nm is read in a microplate reader.

5. Titrimetric assay of lipase activity

Alternatively, lipase activity is determined according to Food Chemical Codex (3rd Ed., 1981, pp 492–493) modified to sunflower oil and pH 5.5 instead of olive oil and pH 6.5. The lipase activity is measured as LUS (lipase units sunflower) where 1 LUS is defined as the quantity of enzyme which can release 1 $\mu$mol of fatty acids per minute from sunflower oil under the above assay conditions.

6. Protein measurement

During the course of purification of lipase as described in the following, the protein eluted from the columns was measured by determining absorbance at 280 nm. The protein in the pooled samples was determined in microtiter plates by a sensitive Bradford method according to Bio-Rad (Bio-Rad Bulletin 1177 EG, 1984). Bovine serum albumin was used as a standard.

EXAMPLE 2

Production, purification and characterization of lipase 3

2.1. Production

A mutant strain of *Aspergillus tubigensis* was selected and used for the production of wild type lipase. This lipase is referred to herein as lipase 3. The strain was subjected to a fermentation in a 750 l fermenter containing 410.0 kg of tap water, 10.8 kg soy flour, 11.1 kg ammonium monohydrogenphosphate, 4.0 kg phosphoric acid (75%), 2.7 kg magnesium sulfate, 10.8 kg sunflower oil and 1.7 kg antifoam 1510. The substrate was heat treated at 121° C. for 45 minutes. The culture media was inoculated directly with $7.5 \times 10^9$ spores of the mutant strain. The strain was cultivated for three days at 38° C., pH controlled at 6.5, aeration at 290 l/min and stirring at 180 rpm the first two days and at 360 rpm the last day. The fermentate was separated using a drum filter and the culture filtrate was concentrated 3.8 times by ultra-filtration. The concentrated filtrate was preserved with potassium sorbate (0.1%) and sodium benzoate (0.2%) and used as a starting material for purification of lipase.

2.2. Purification of lipase

A 60 ml sample of ferment (cf. 2.1) containing 557 LUS/ml, pH 5.5 was first filtered through a GF/B filter and subsequently through a 0.45 $\mu$m filter. The filtered sample was desalted using a Superdex G25 SP column (430 ml, 22×5 cm) equilibrated in 20 mM triethanolamine, pH 7.3. The flow rate was 5 ml/min. The total volume after desalting was 150 ml.

The desalted sample was applied to a Source Q30 anion exchanger column (100 ml, 5×5 cm) equilibrated in 20 mM triethanolamine, pH 7.3. The column was washed with equilibration buffer until a stable baseline was obtained. Lipase activity was eluted with a 420 ml linear gradient from 0 to 0.35 M sodium chloride in equilibration buffer, flow rate 5 ml/min. Fractions of 10 ml were collected. Sodium acetate (100 $\mu$l of a 2M solution) was added to each fraction to adjust pH to 5.5. Fractions 26–32 (70 ml) were pooled.

To the pool from the anion exchange step was added ammonium sulfate to 1 M and the sample was applied to a Source Phenyl HIC column (20 ml, 10×2 cm) equilibrated in 20 mM sodium acetate (pH 5.5), 1 M ammonium sulfate. The column was washed with the equilibration buffer. Lipase was eluted with a 320 ml linear gradient from 1 M to 0 M ammonium sulfate in 20 mM sodium acetate (pH 5.5), flow 1.5 ml/min. Fractions of 7.5 ml were collected.

Fractions 33–41 were analyzed by SDS-PAGE using a NOVEX system with precast gels. Both electrophoresis and silver staining of the gels were done according to the manufacturer (Novex, San Diego, USA). (The same system was used for native electrophoresis and isoelectric focusing). It was found that fraction 40 and 41 contained lipase as the only protein.

2.3. Characterization of the purified lipase (i) Determination of molecular weight The apparent molecular weight of the native lipase was 37.7 kDa as measured by the above SDS-PAGE procedure. The purified lipase eluted at a molecular weight of 32.2 kDa from a Superose 12 gel filtration column (50 mM sodium phosphate, 0.2 M sodium chloride, pH 6.85, flow 0.65 ml/min) and is therefore a monomer.

The molecular weight of the lipase was also determined by matrix-assisted laser desorption ionisation (MALDI) by means of a time-of-flight (TOF) mass spectrometer (Voyager Bio-Spectrometry Workstation, Perspective Biosystems). Samples were prepared by mixing 0.7 µl of desalted lipase solution and 0.7 µl of a matrix solution containing sinapic acid (3.5-dimethoxy-4-hydroxy cinnamic acid) in 70% acetonitrile (0.1% TFA, 10 mg/ml). 0.7 µl of the sample mixture was placed on top of a stainless steel probe tip and allowed to air-dry prior to introduction into the mass spectrometer. Spectra were obtained from at least 100 laser shots and averaged to obtain a good signal to noise ratio. The molecular mass for the lipase was found to be 30,384 Da and 30,310 Da by two independent analyses.

Digestion of the lipase with endo-β-N-acetylglucosamidase H (10 µl) from Streptomyces (Sigma) was carried out by adding 200 µl lipase and incubating at 37° C. for 2 hours. The digestion mixture was desalted using a VSWP filter and analyzed directly by MALDI mass spectrometry. A major component of deglycosylated lipase gave a mass of 29,339 Da and 29,333 Da by two independent analyses. A minor component with a mass of 29,508 Da was also observed. These values corresponds well to the later calculated theoretical value of 28,939 Da based on the complete amino acid sequence of the mature lipase.

(ii) Determination of the isoelectric point

The isoelectric point (pI) for the lipase was determined by isoelectric focusing and was found to be 4.1.

A calculation of the pI based on the amino acid sequence as determined in the following and shown as SEQ ID NO: 9 gave an estimated pI of 4.07.

(iii) Determination of temperature stability

Eppendorf tubes with 25 µl of purified lipase 3 plus 50 µl 100 mM sodium acetate buffer (pH 5.0) were incubated for 1 hour in a water bath at respectively 30, 40, 50, and 60° C. A control was treated in the same way, but left at room temperature. After 1 hour the lipase 3 activity was determined by the p-nitrophenyl acetate assay as described above.

The purified lipase had a good thermostability. It was found that the lipase maintained 60% of its activity after 1 hour at 60° C. 80% and 85% activity was maintained after 1 hour at 50° C. and 40° C. respectively.

(iv) Determination of pH stability

Purified lipase 3 (200 µl) was added to 5 ml of 50 mM buffer solutions: (sodium phosphate, pH 8.0, 7.0 and 6.0 and sodium acetate pH 5.0, 4.0 and 3.5). The control was diluted in 5 ml of 4 mM sodium acetate pH 5.5. After four days at room temperature the residual activity was measured by the Modified Food Chemical Codex assay for lipase activity as described above. The lipase was very stable in the pH range from 4.0 to 7.0 where it maintained about 100% activity relative to the control (Table 2.1). At pH 3.5 the lipase maintained 92% activity, and at pH 8.0 95% residual activity was maitained as compared to the control.

TABLE 2.1 pH stability of lipase 3

| pH | Activity (LUT/ml) | Activity (%) |
|---|---|---|
| Control (pH 5.5) | 89.2 | 100 |
| 3.5 | 82.5 | 92 |
| 4.0 | 91.7 | 103 |
| 5.0 | 86.5 | 97 |
| 6.0 | 92.4 | 104 |
| 7.0 | 90.6 | 102 |
| 8.0 | 84.4 | 95 |

EXAMPLE 3

Amino acid sequencing of lipase 3

Purified lipase enzyme was freeze-dried and 100 µg of the freeze-dried material was dissolved in 50 µl of a mixture of 8 M urea and 0.4 M ammonium hydrogencarbonate, pH 8.4. The dissolved protein was denatured and reduced for 15 minutes at 50° C. following overlay with nitrogen and addition of 5 µl 45 mM dithiothreitol. After cooling to room temperature, 5 µl of 100 mM iodoacetamide was added for the cysteine residues to be derivatized for 15 minutes at room temperature in the dark under nitrogen.

135 µl of water and 5 µg of endoproteinase Lys-C in 5 µl of water was added to the above reaction mixture and the digestion was carried out at 37° C. under nitrogen for 24 hours. The resulting peptides were separated by reverse phase HPLC on a VYDAC C18 column (0.46×15 cm; 10 µm; The Separation Group, California, USA) using solvent A: 0.1% TFA in water and solvent B: 0.1% TFA in acetonitrile. Selected peptides were rechromatographed on a Develosil C18 column (0.46×10 cm, Novo Nordisk, Bagsværd, Denmark) using the same solvent system, prior to N-terminal sequencing. Sequencing was done using an Applied Biosystems 476A sequencer using pulsed-liquid fast cycles according to the manufacturer's instructions (Applied Biosystems, California, USA).

For direct N-terminal sequencing, the purified protein was passed through a Brownlee C2 Aquapore column (0.46×3 cm, 7 µm, Applied Biosystems, California, USA) using the same solvent system as above. N-terminal sequencing was then performed as described above. As the protein was not derivatized prior to sequencing, cysteine residues could not be determined.

The following peptide sequences were found:

N-terminal: Ser-Val-Ser-Thr-Ser-Thr-Leu-Asp-Glu-Leu-Gln-Leu-Phe-Ala-Gln-Trp-Ser-Ala-Ala-Ala-Tyr-X-Ser-Asn-Asn (SEQ ID NO:1)

Internal peptide 1: Val-His-Thr-Gly-Phe-Trp-Lys (SEQ ID NO:2)

Internal peptide 2: Ala-Trp-Glu-Ser-Ala-Ala-Asp-Glu-Leu-Thr-Ser-Lys-Ile-Lys (SEQ ID NO:3)

No further peptides could be purified from the HPLC fractionation assumingly because they were very hydrophobic and therefore tightly bound to the reverse phase column.

A search in SWISS-PROT database release 31 for amino acid sequences with homology to the above peptides was performed and only three sequences were found.

All of the above peptides showed a low homology to the above known sequences. Especially internal peptide 2 has very low homology to the three lipases, (SEQ ID NO:10), (SEQ ID NO:11) and MDLA-(SEQ ID NO:12) from *Rhizopus delamar* (Haas and Berka, Gene, 1991, 109:107–113), *Rhizomucor miehei* (Boel et al., Lipids, 1988, 23:701–706) and *Penicillium camenbertii* (Yamaguchi et al., Gene, 1991, 103:61–67; Isobe and Nokihara, Febs. Lett., 1993, 320:101–106) respectively. Although the homology was not very high it was possible to position the lipase 3 peptides on these sequences as it is shown in the below Table 3.1.

TABLE 3.1

Alignment of lipase 3 peptides with known lipase sequences

```
(SEQ ID      LIP_RHIDL   MVSFISISQGVSLCLLVSSMMLGSSAVPVSGKSGSSNTAVSASDNAALPP    50
NO:10)

(SEQ ID      LIP_RHIMI   MVLKQRANYLGFLIVFFTAFLV--EAVPIKRQSNSTVDS--------LPP    40
NO:11)

(SEQ ID      MDLA_PENCA  MRLS-----------FFTAL------------------SAVASLGYALPG    21
NO:12)

*         . ...              .         **

(SEQ ID NO:1) N-Terminal              SVSTSTLDELQLFAQWSAAAYXSNN

LIP_RHIDL   LISSRCAPPSNKGSKSDLQAEPYNMQKNTEWYESHGGNLTSIGKRDDNLV   100

LIP_RHIMI   LIPSRTSAPSSSPSTTDPEAPAM----------SRNGPLPS----DVETK    76

MDLA_PENCA  KLQSR------DVSTSELDQFEFWVQYAAASY------------------    47

. **         . *... ..

LIP_RHIDL   GGMTLDLPSDAPPISLSSSTNSASDGGKVVAATTAQIQEFTKYAGIAATA   150

LIP_RHIMI   YGMALNATSYPDSV-----VQAMSIDGGIRAATSQEINELTYYTTLSANS   121

MDLA_PENCA  -------------------------------------YEADYTAQVGDKL    60

*  .  . ....

LIP_RHIDL   YCRSVVPGNKWDCVQCQKWVPDGKIITTFT-SLLSDTNGYVLRSDKQKTI   199

LIP_RHIMI   YCRTVIPGATWDCIHCDA-TEDLKIIKTWS-TLIYDTNAMVARGDSEKTI   169

MDLA_PENCA  SCSKG------NCPEVEA--TGATVSYDFSDSTITDTAGYLAVDHTNSAV   102

*..         .*  . .   . ..  ... . **... .  .......

(SEQ ID NO:2) Peptide 1                            VHTGFWK
(SEQ ID NO:3) Peptide 2                                   AWESAADELTSK

LIP_RHIDL   YLVFRGTNSFRSAITDIVFNFSDYKPVKGAKVHAGFLSSYEQVVNDYFPV   249

LIP_RHIMI   YIVFRGSSSIRNWIADLTFVPVSYPPVSGTKVHKGFLDSYGEVQNELVAT   219

MDLA_PENCA  VLAFRGSYSVRNWVADATFVHTNPGLCDGCLAELGFWSSWKLVRDDIIKE   152

..***. * *.  ..* .*     .   .*  .. ** ...   ...

Peptide 2   IK
             (cont.)

LIP_RHIDL   VQEQLTAHPTYKVIVTGHSLGGAQALLAGMDLYQREPRLSPKNLSIFTVG   299

LIP_RHIMI   VLDQFKQYPSYKVAVTGHSLGGATALLCALDLYQREEGLSSSNLFLYTQG   269

MDLA_PENCA  LKEVVAQNPNYELVVVGHSLGAAVATLAATDL--RGKGYPSAKLYAYA--   198

. .   . *.*.. *.*****.* * * . **  *.   ...* ..

LIP_RHIDL   GPRVGNPTFAYYVESTGIPFQRTVHKRDIVPHVPPQSFGFLHPGVESWIK   349

LIP_RHIMI   QPRVGDPAFANYVVSTGIPYRRTVNERDIVPHLPPAAFGFLHAGEEYWIT   319

MDLA_PENCA  SPRVGNAALAKYITAQGNNF-RFTHTNDPVPKLPLLSMGYVHVSPEYWIT   247

****....* *. . *   . *  ....* **..*  ..*...* . * **.

LIP_RHIDL   SGTSN-V-----QICTSEIETKDCSNSIVPFTSILD-HLSYF-DINEGSC   391

LIP_RHIMI   DNSPETV-----QVCTSDLETSDCSNSIVPFTSVLD-HLSYF-GINTGLC   362

MDLA_PENCA  SPNNATVSTSDIKVIDGDVSFDGNTGTGLPLLTDFEAHIWYFVQVDAGKG   297

. ...*     .. ..... .. .... .*. ... *. **  ...*

LIP_RHIDL   -------L                                             392
```

TABLE 3.1-continued

Alignment of lipase 3 peptides with known lipase sequences

```
LIP_RHIMI    -------T                                    363

MDLA_PENCA  PGLPFKRV                                     305
```

EXAMPLE 4

Isolation and purification of *Aspergillus tubigensis* genomic DNA

The *Aspergillus tubigensis* mutant strain was grown in PDB (Difco) for 72 hours and the mycelium was harvested. 0.5–1 g of mycelium was frozen in liquid nitrogen and ground in a mortar. Following evaporation of the nitrogen, the ground mycelium was mixed with 15 ml of an extraction buffer (100 nM Tris.HCl, pH 8.0, 50 mM EDTA, 500 mM NaCl, 10 mM β-mercaptoe-thanol) and 1 ml 20% sodium dodecylsulfate. The mixture was vigorously mixed and incubated at 65° C. for 10 min. 5 ml 3M potassium acetate, (pH 5.1 adjusted with glacial acetic acid) was added and the mixture further incubated on ice for 20 min. The cellular debris was removed by centrifugation for 20 min. at 20,000×g and 10 ml isopropanol was added to the supernatant to precipitate (30 min at −20° C.) the extracted DNA. After further centrifugation for 15 min at 20,000×g, the DNA pellet was dissolved in 1 ml TE (10 mM Tris.HCl pH 8.0, 1 mM EDTA) and precipitated again by addition of 0.1 ml 3 M NaAc, pH 4.8 and 2.5 ml ethanol. After centrifugation for 15 min at 20,000×g the DNA pellet was washed with 1 ml 70% ethanol and dried under vacuum. Finally, the DNA was dissolved in 200 μl TE and stored at −20° C.

EXAMPLE 5

The generation of a fragment of the putative gene coding for lipase 3 using PCR

To obtain a fragment of the putative gene (in the following referred to as the lipA gene) as a tag to isolate the complete gene, a PCR amplification procedure based on the information in the isolated peptide sequences was carried out.

Degenerated primers for PCR amplification of a fragment of the lipase gene were designed based on the amino acid sequences of the isolated peptides. The following three PCR primers were synthesised:

C035: TTC CAR AAN CCN GTR TGN AC (SEQ ID NO:4) 20 mer 256 mixture, based on peptide 1 sequence VHTGFWK (SEQ ID NO:2) (Reversed).

C036: CAR YTN TTY GCN CAR TGG (SEQ ID NO:5) 18 mer 256 mixture, based on the N-terminal sequence QLFAQW.

C037: GCV GCH SWY TCC CAV GC (SEQ ID NO:6) 17 mer 216 mixture, based on internal peptide 2 sequence AWESAA (reversed).

The oligonucleotides were synthesised on a Applied Biosystems model 392 DNA/RNA Synthesizer. To reduce the degree of degeneracy the rare Ala codon GCA and the Ser codon TCA have been excluded in design of primer C037.

With these primers the desired fragments were amplified by PCR. Using these primers it was expected that a fragment of about 300 bp should be amplified provided there are no introns in the fragment.

The following PCR reactions were set up in 0.5 ml PCR tubes to amplify a putative lipA fragment:

1. 0.5 μg total genomic DNA,
   100 pmol primer C036,
   100 pmol primer C037,
   10 μl PCR Buffer II (Perkin Elmer),
   6 μl 25 mM MgCl$_2$,
   2 μl dNTP mix (10 mM dATP, 10 mM dCTP, 10 mM dGTP, 10 mM dTTP),
   2 units Amplitaq polymerase (Perkin Elmer), and water to a total volume of 100 μl.

2. 0.5 μg total genomic DNA,
   100 pmol primer C035,
   100 pmol primer C036,
   10 μl PCR Buffer II (Perkin Elmer),
   6 μl 25 mM MgCl$_2$,
   2 μl dNTP mix (10 mM DATP, 10 mM dCTP, 10 mM dGTP, 10 mM dTTP),
   2 units Amplitaq polymerase (Perkin Elmer), and water to a total volume of 100 μl.

The reactions were performed using the following program:

94° C. 2 min

94° C. 1 min)

40° C. 1 min)

72° C. 1 min) These three steps were repeated for 30

72° C. 5 min cycles

5° C. SOAK

The PCR amplifications were performed in a MJ Research Inc. PTC-100 Thermocycler.

In reaction 1, three distinct bands of about 300, 360 and 400 bp, respectively could be detected. These bands were isolated and cloned using the pT7-Blue-T-vector kit (Novagene). The sizes of these fragment is in agreement with the expected size provided that the fragment contains 0, 1 or 2 introns, respectively.

The three fragments were sequenced using a "Thermo Sekvenase fluorescent labelled primer cycle sequencing Kit" (Amersham) and analyzed on a ALF sequencer (Pharmacia) according to the instructions of the manufacturer. The fragment of about 360 bp contained a sequence that was identified as a lipase and, as it contained the part of the N-terminal distal to the sequence used for primer design, it was concluded that the desired lipA gene fragment was obtained.

The sequence of the about 360 bp PCR fragment (SEQ ID NO:7) is shown in the following Table 5.1 (SEQ ID NO: 13). The four amino acid fragments of Table 5.1 are contained in SEQ ID NOS; 14, 15, 16, and 17. The peptide sequence used for primer design is underlined. The remaining part of the N-terminal sequence is doubly underlined.

TABLE 5.1

PCR-generated putative lipA sequence

```
         10        20        30        40        50        60
          |         |         |         |         |         |
tacccggggntccgattCAGTTGTTCGCGCAATGGTCTGCCGCAGCTTATTGCTCGAATA

O  L  F  A  O  W  S  A  A  A  Y  C  X  N 70        80        90       100       110       120
          |         |         |         |         |         |
ATATCGACTCGAAAGAVTCCAACTTGACATGCACGGCCAACGCCTGTCCATCAGTCGAGG

N  I  D  S  K  X  S  N  L  T  C  T  A  N  A  C  P  S  V  E 130       140       150       160       170       180
          |         |         |         |         |         |
AGGCCAGTACCACGATGCTGCTGGAGTTCGACCTGTATGTCACTCAGATCGCAGACATAG

E  A  S  T  T  M  L  L  E  F  D  L  Y  V  T  Q  I  A  D  I 190       200       210       220       230       240
          |         |         |         |         |         |
AGCACAGCTAATTGAACAGGACGAACGACTTTTGGAGGCACAGCCGGTTTCCTGGCCGCG

E  H  S  -  L  N  R  T  N  D  F  W  R  H  S  R  F  P  G  R 250       260       270       280       290       300
          |         |         |         |         |         |
GACAACACCAACAAGCGGCTCGTGGTCGCCTTCCGGGGAAGCAGCACGATTGAGAACTGG

G  Q  H  Q  Q  A  A  R  G  R  L  P  G  K  Q  H  D  -  E  L 310       320       330
          |         |         |
ATTGCTAATCYTGACTTCATCCTGGRAGATAACG

D  C  -  X  -  L  H  P  X  R  -
```

The finding of this sequence permitted full identification of the PCR fragment as part of the lipA gene. The stop codon found in the reading frame can be caused either by a PCR or a reading error or there can be an intron encoded in the fragment as a consensus intron start and ending signal (shown in bold). If the putative intron is removed a shift in reading frame will occur. However, an alignment of the deduced amino acid sequence and the fungal lipases shown in Table 3.1 suggested that the fragment was part of the desired gene.

EXAMPLE 6

Cloning and characterisation of the lipA gene (i) Construction of an *Aspergillus tubigensis* genomic library

*Aspergillus tubigensis* genomic DNA was digested partially with Tsp5091 (New England Biolabs Inc.). 10 μg DNA was digested in 100 μl reaction mixture containing 2 units Tsp5091. After 5, 10, 15 and 20 minutes 25 μl was removed from the reaction mixture and the digestion was stopped by addition of 1 μl 0.5 M EDTA, pH 8.0. After all four reactions had been stopped, the samples were run on a it agarose gel in TAE buffer (10×TAE stock containing per liter: 48.4 g Trizma base, 11.5 ml glacial acetic acid, 20 ml 0.5 M EDTA pH 8.0). HindIII-digested phage Lambda DNA was used as molecular weight marker (DNA molecular weight marker II, Boehringer, Mannheim). Fragments of a size between about 5 and 10 kb were cut out of the gel and the DNA fragments were purified using Gene Clean II Kit (Bio-101 Inc.). The purified fragments were pooled and 100 ng of the pooled fragments were ligated into 1 μg EcoRI-digested and dephosphorylated ZAP II vector (Stratagene) in a total volume of 5 μl. 2 μl of this volume was packed with Gigapack II packing extract (Stratagene) which gave a primary library of 650,000 pfu.

*E. coli* strain XL1-Blue-MRF (Stratagene) was infected with 5×50,000 pfu of the primary library. The infected bacteria were mixed with top agarose (as NZY plates but with 6 g agarose per liter instead of the agar) and plated on 5 NZY plates (13 cm). After incubation at 37° C. for 7 hours, 10 ml SM buffer (per liter: 5.8 g NaCl, 2.0 g $MgCl_2.7H_2O$, 50 ml 1 M Tris.HCl pH 7.5, 5.0 ml of 2% (w/v) gelatine) and incubated overnight at room temperature with gently shaking. The buffer containing washed-out phages was collected and pooled. 5% chloroform was added and after vigorous mixing the mixture was incubated 1 hour at room temperature. After centrifugation for 2 minutes at 10,000×g the upper phase containing the amplified library was collected and dimethylsulphoxide was added to 7%. Aliquots of the library was taken out in small tubes and frozen at −80° C. The frozen library contained $2.7 \times 10^9$ pfu/ml with about 6% without inserts.

(ii) Screening of the *Aspergillus tubigensis* library

2×50.000 pfu were plated on large (22×22 cm) NZY plates containing a medium containing per liter: 5 g NaCl, 2 g $MgSO_4.7H_2O$, 5 g yeast extract, 10 g casein hydrolysate, 15 g agar, pH adjusted to 7.5 with NaOH. The medium was autoclaved and cooled to about 60° C. and poured into the plates. Per plate was used 240 ml of medium.

The inoculated NZY plates were incubated overnight at 37° C. and plaque lifts of the plates were made. Two lifts were made for each plate on Hybond N (Amersham) filters. The DNA was fixed using UV radiation for 3 min. and the filters were hybridized as described in the following using, as the probe, the above PCR fragment of about 360 bp that was labelled with $^{32}$P-dCTP using Ready-to-Go labelling kit (Pharmacia).

The filters were prehybridised for one hour at 65° C. in 25 ml prehybridisation buffer containing 6.25 ml 20×SSC (0.3 M Na$_3$citrate, 3 M NaCl), 1,25 ml 100×Denhard solution, 1.25 ml 10% SDS and 16.25 ml water. 150 µl 10 mg/ml denatured Salmon sperm DNA was added to the prehybridization buffer immediately before use. Following prehybridization, the prehybridisation buffer was discarded and the filters hybridised overnight at 65° C. in 25 ml prehybridisation buffer with the radiolabelled PCR fragment.

Next day the filters were washed according to the following procedure: 2×15 min. with 2×SSC+0.1% SDS, 15 min. with 1×SSC+0.1% SDS and 10 min. with 0.1×SSC+0.1% SDS.

All washes were done at 65° C. The sheets were autoradiographed for 16 hours and positive clones were isolated. A clone was reckoned as positive only if there was a hybridisation signal on both plaque lifts of the plate in question.

Seven putative clones were isolated and four were purified by plating on small petri dishes and performing plaque lifts essentially as described above.

The purified clones were converted to plasmids using an ExAssist Kit (Stratagene).

Two sequencing primers were designed based on the about 360 bp PCR fragment. The sequencing primers were used to sequence the clones and a positive clone with the lipA gene encoding lipase 3 was found. The isolated positive clone was designated pLIP4.

(iii) Characterisation of the pLIP4 clone

A restriction map of the clone was made. The above 360 bp PCR fragment contained a SacII site and as this site could be found in the genomic clone as well this site facilitated the construction of the map. The restriction map showing the structure of pLIP4 is shown in FIG. 1. The restriction map shows that the complete gene is present in the clone. Additionally, since promoter and terminator sequences are present, it was assumed that all the important regions is present in the clone.

A sample of *Escherichia coli* strain DH5α containing pLIP4 was deposited in accordance with the Budapest Treaty with The National Collections of Industrial and Marine Bacteria Limited (NCIMB) at 23 St. Machar Drive, Aberdeen, Scotland, United Kingdom, AB2 1RY on Feb. 24, 1997 under the accession number NCIMB 40863.

The gene was sequenced using cycle sequencing and conventional sequencing technology. The complete sequence is shown below in Table 6.1 (SEQ ID NO: 18). The sequence has been determined for both strands for the complete coding region and about 100 bp upstream and downstream of the coding region. The sequences downstream to the coding region have only been determined on one strand and contains a few uncertainties. In the sequence as shown below, the intron ences are indicated as lowercase letters and the N-terminal and the two internal peptides (peptide 1 and peptide 2) are underlined:

TABLE 6.1.

The DNA seauence for the lipA gene and flanking sequences (SEQ ID NO:18)

```
  1 CCNDTTAATCCCCCACCGGGGTTCCCGCTCCCGGATGGAGATGGGGCCAAAACTGGCAAC

61 CCCCAGTTGCGCAACGGAACAACCGCCGACCCGGAACAAAGGATGCGGATGAGGAGATAC

121 GGTGCCTGATTGCATGGCTGGCTTCATCTGCTATCGTGACAGTGCTCTTTGGGTGAATAT

181 TGTTGTCTGACTTACCCCGCTTCTTGCTTTTTCCCCCCTGAGGCCCTGATGGGGAATCGC

241 GGTGGGTAATATGATATGGGTATAAAAGGGAGATCGGAGGTGCAGTTGGATTGAGGCAGT

301 GTGTGTGTGTGCATTGCAGAAGCCCGTTGGTCGCAAGGTTTTGGTCGCCTCGATTGTTTG

361 TATACCGCAAGATGTTCTCTGGACGGTTTGGAGTGCTTTTGACAGCGCTTGCTGCGCTGG
                                              M  F  S  G  R  F  G  V  L  L  T  A  L  A  A  L

421 GTGCTGCCGCGCCGGCACCGCTTGCTGTGCGGAgtaggtgtgcccgatgtgagatggttg
     G  A  A  A  P  A  P  L  A  V  R 481 gatagcactgatgaagggtgaatagGTGTCTCGACTTCCACGTTGGATGAGTTGCAATTG
                              S  V  S  T  S  T  L  D  E  L  Q  L 541 TTCGCGCAATGGTCTGCCGCAGCTTATTGCTCGAATAATATCGACTCGAAAGACTCCAAC
     F  A  Q  W  S  A  A  A  Y  C  S  N  N  I  D  S  K  D  S  N 601 TTGACATGCACGGCCAACGCCTGTCCATCAGTCGAGGAGGCCAGTACCACGATGCTGCTG
     L  T  C  T  A  N  A  C  P  S  V  E  E  A  S  T  T  M  L  L 661 GAGTTCGACCTgtatgtcactcagatcgcagacatagagcacagctaatttgaacagGAC
     E  F  D  L                                              T
```

TABLE 6.1.-continued

The DNA sequence for the lipA gene and flanking sequences (SEQ ID NO:18)

```
 721 GAACGACTTTGGAGGCACAGCCGGTTTCCTGGCCGCGGACAACACCAACAAGCGGCTCGT
       N  D  F  G  G  T  A  G  F  L  A  A  D  N  T  N  K  R  L  V

781 GGTCGCCTTCCGGGGAAGCAGCACGATTGAGAACTGGATTGCTAATCTTGACTTCATCCT
       V  A  F  R  G  S  S  T  I  E  N  W  I  A  N  L  D  F  I  L

841 GGAAGATAACGACGACCTCTGCACCGGCTGCAAGGTCCATACTGGTTTCTGGAAGGCATG
       E  D  N  D  D  L  C  T  G  C  K  V  H  T  G  F  W  K  A  W

901 GGAGTCCGCTGCCGACGAACTGACGAGCAAGATCAAGTCTGCGATGAGCACGTATTCGGG
       E  S  A  A  D  E  L  T  S  K  I  K  S  A  M  S  T  Y  S  G

961 CTATACCCTATACTTCACCGGGCACAGTTTGGGCGGCGCATTGGCTACGCTGGGAGCGAC
       Y  T  L  Y  F  T  G  H  S  L  G  G  A  L  A  T  L  G  A  T

1021 AGTTCTGCGAAATGACGGATATAGCGTTGAGCTGgtgagtccttcacaaaggtgatggag
       V  L  R  N  D  G  Y  S  V  E  L 1081 cgacaatcgggaacagacagtcaatagTACACCTATGGATGTCCTCGAATCGGAAACTAT
                                    Y  T  Y  G  C  P  R  I  G  N  Y 1141 GCGCTGGCTGAGCATATCACCAGTCAGGGATCTGGGGCCAACTTCCGTGTTACACACTTG
       A  L  A  E  H  I  T  S  Q  G  S  G  A  N  F  R  V  T  H  L 1201 AACGACATCGTCCCCCGGGTGCCACCCATGGACTTTGGATTCAGTCAGCCAAGTCCGGAA
       N  D  I  V  P  R  V  P  P  M  D  F  G  F  S  Q  P  S  P  E 1261 TACTGGATCACCAGTGGCAATGGAGCCAGTGTCACGGCGTCGGATATCGAAGTCATCGAG
       Y  W  I  T  S  G  N  G  A  S  V  T  A  S  D  I  E  V  I  E 1321 GGAATCAATTCAACGGCGGGAAATGCAGGCGAAGCAACGGTGAGCGTTGTGGCTCACTTG
       G  I  N  S  T  A  G  N  A  G  E  A  T  V  S  V  V  A  H  L 1381 TGGTACTTTTTTGCGATTTCCGAGTGCCTGCTATAACTAGACCGACTGTCAGATTAGTGG
       W  Y  F  F  A  I  S  E  C  L  L  -

1441 ACGGGAGAAGTGTACATAAGTAATTAGTATATAATCAGAGCAACCCAGTGGTGGTGATGG

1501 TGGTGAAAGAAGAAACACATTGAGTTCCCATTACGKAGCAGWTAAAGCACKTKKGGAGGC

1561 GCTGGTTCCTCCACTTGGCAGTTGGCGGCCATCAATCATCTTTCCTCTCCTTACTTTCGT

1621 CCACCACAACTCCCATCCTGCCAGCTGTCGCATCCCCGGGTTGCAACAACTATCGCCTCC

1681 GGGGCCTCCGTGGTTCTCCTATATTATTCCATCCGACGGCCGACGTTTCACCCTCAACCT

1741 GCGCCGCCGCAAAATCTCCCCGAGTCGGTCAACTCCCTCGAACCGCCGCCCGCATCGACC

1801 TCACGACCCCGACCGTCTGYGATYGTCCAACCG
```

(iv) Analysis of the sequence of the complete gene

The peptide sequences obtained could all be found in the deduced amino acid sequence (see Table 5.1) which confirms again that the sequence found is the sequence of the lipase 3 gene. The gene was designated lipA.

The amino acid sequence was aligned with the three fungal lipases used to align the peptide sequences. The alignment is shown in Table 6.2.

TABLE 6.2

Alignment of the lipase 3 sequence with known fungal lipases

```
LIPASE3    MFSG-------------RFGVLL-----------------TALAA    15
MDLA_PENCA MRLS-------------FFTAL------------------SAVAS    14
LIP_RHIDL  MVSFISISQGVSLCLLVSSMMLGSSAVPVSGKSGSSNTAVSASDNAALPP 50
LIP_RHIMI  MVLKQRANYLGFLIVFFTAFLV--EAVPIKRQSNSTVDS--------LPP 40
           *                 ..                    ...

LIPASE3    L-------------------------------------------------- 16
MDLA_PENCA L--------------------------------------------------  15
LIP_RHIDL  LISSRCAPPSNKGSKSDLQAEPYNMQKNTEWYESHGGNLTSIGKRDDNLV 100
LIP_RHIMI  LIPSRTSAPSSSPSTTDPEAPAM----------SRNGPLPS----DVETK  76
           *

LIPASE3    --------GAAAPAPLA-----------VRSVSTSTLDELQLFAQWSAAA  47
MDLA_PENCA --------GYALPGKLQ-----------SRDVSTSELDQFEFWVQYAAAS  46
LIP_RHIDL  GGMTLDLPSDAPPISLSSSTNSASDGGKVVAATTAQIQEFTKYAGIAATA 150
LIP_RHIMI  YGMALNATSYPDSV-----VQAMSIDGGIRAATSQEINELTYYTTLSANS 121
                    . . .              ....  ....  ..  .*..

LIPASE3    YCSNNIDSK-DSNLTCTANACPSVEEASTTMLLEFDLTNDFGGTAGFLAA  96
MDLA_PENCA YYEADYTAQVGDKLSCSKGNCPEVEATGATVSYDFS-DSTITDTAGYIAV  95
LIP_RHIDL  YCRSVVP---GNKWDCVQ--CQKWVPDGKIIT---TFTSLLSDTNGYVLR 192
LIP_RHIMI  YCRTVIP---GATWDCIH--CDA-TEDLKIIK---TWSTLIYDTNAMVAR 162
           *. .      ... .*    *       .      .   .  .*.. .

LIPASE3    DNTNKRLVVAFRGSSTIENWIANLDFILEDNDDLCTGCKVHTGFWKAWES 146
MDLA_PENCA DHTNSAVVLAFRGSYSVRNWVADATFV-HTNPGLCDGCLAELGFWSSWKL 144
LIP_RHIDL  SDKQKTIYLVFRGTNSFRSAITDIVFNFSDYKPV-KGAKVHAGFLSSYEQ 241
LIP_RHIMI  GDSEKTIYIVFRGSSSIRNWIADLTFVPVSYPPV-SGTKVHKGFLDSYGE 211
           ..... . ...***..    .... *   .  . .* .. ** ...

LIPASE3    AADELTSKIKSAMSTYSGYTLYFTGHSLGGALATLGATVL--RNDGY-SV 193
MDLA_PENCA VRDDIIKELKEVVAQNPNYELVVVGHSLGAAVATLAATDL--RGKGYPSA 192
LIP_RHIDL  VVNDYFPVVQEQLTAHPTYKVIVTGHSLGGAQALLAGMDLYQREPRLSPK 291
LIP_RHIMI  VQNELVATVLDQFKQYPSYKVAVTGHSLGGATALLCALDLYQREEGLSSS 261
           . ...    . .    ..*..  .*****.* * * . *  *.   .

LIPASE3    ELYTY--GCPRIGNYALAEHITSQGSGANFRVTHLNDIVPRVPPMDFGFS 241
MDLA_PENCA KLYAY--ASPRVGNAALAKYITAQGN--NFRFTHTNDPVPKLPLLSMGYV 238
LIP_RHIDL  NLSIFTVGGPRVGNPTFAYYVESTGIPFQ-RTVHKRDIVPHVPPQSFGFL 340
LIP_RHIMI  NLFLYTQGQPRVGDPAFANYVVSTGIPYR-RTVNERDIVPHLPPAAFGFL 310
           .*  . . **.*. ...*  ...  *   . *  ...*  **...*  ..*.

LIPASE3    QPSPEYWITSGNGASVTASDIEVIEGINSTAGNAGEATVSVV---AHLWY 288
MDLA_PENCA HVSPEYWITSPNNATVSTSDIKVIDGDVSFDGNTGTGLPLLTDFEAHIWY 288
LIP_RHIDL  HPGVESWIKSGTSN-VQICTSEIE------TKDCSNSIVPFTSILDHLSY 383
LIP_PHINI  HAGEEYWITDNSPETVQVCTSDLE------TSDCSNSIVPFTSVLDHLSY 354
           . . * **.. . . *  .. ..     . . ...   . .*. .

LIPASE3    FFAISECL--------L                                 297
MDLA_PENCA FVQVDAGKGPGLPFKPV                                 305
LIP_RHIDL  F-DINEGSC-------L                                 392
LIP_RHIMI  F-GINTGLC-------T                                 363
           *   ...
```

The above alignment shows that lipase 3 is homologous to the known lipase sequences but that the homology is not very high. Deletions or insertions in the lipase 3 sequence was not observed when comparing the sequence with these three lipases. This strengthens the probability that the putative introns have been identified correctly.

A search in SWISS-PROT release 31 database was performed and it did not lead to further sequences with higher homology than that to the above known lipases (Table 6.3).

The sequence with highest homology is a mono- diacyl lipase from *Penicillium camembertii* where the identity is found to 42%. However the C- terminal of lipase 3 resembles the 2 lipases from Zygomycetes (Rhizopus and Rhizomucor) and not the *P. camembertii* enzyme.

TABLE 6.3

Alignment of coding sequences of the lipA gene and gene coding for mono-diacyl lipase from Penicillium camemberti

```
   LIPASE3-  MFSGRFGVLLTALAALGAAAPAPLAVRSVSTSTLDELQLFAQWSAAAYCS  -50
             |   |   | ||||| |   |  ||||  ||       |   ||  |
MDLA_PENCA-  MRLSFFTAL-SAVASLGYALPGKLQSRDVSTSELDQFEFWVQYAAASYYE -49

LIPASE3-  NNIDSK-DSNLTCTANACPSVEEASTTMLLEFDLTNDFGGTAGFLAADNT  -99
             | |     ||  ||       |      |         |||   | | |
MDLA_PENCA-  ADYTAQVGDKLSCSKGNCPEVEATGATVSYDFS-DSTITDTAGYIAVDHT  -98

LIPASE3-  NKRLVVAFRGSSTIENWIANLDFILEDNDDLCTGCKVHTGFWKAWESAAD -149
             |   | ||||||    ||| |    |    ||||    |||    |    |
MDLA_PENCA-  NSAVVLAFRGSYSVRNWVADATFV-HTNPGLCDGCLAELGFWSSWKLVRD -147

LIPASE3-  ELTSKIKSAMSTYSGYTLYFTGHSLGGALATLGATVLRNDGY-SVELYTY -198
                         |  |     ||||| | |||  || ||   ||   |  |||
MDLA_PENCA-  DIIKELKEVVAQNPNYELVVVGHSLGAAVATLAATDLRGKGYPSAKLYAY -197

LIPASE3-  GCPRIGNYALAEHITSQGSGANFRVTHLNDIVPRVPPMDFGFSQPSPEYW -248
             || || |||  || || |    ||| || || ||       |       | ||||||
MDLA_PENCA-  ASPRVGNAALAKYITAQGN--NFRFTHTNDPVPKLPLLSMGYVHVSPEYW -245

LIPASE3-  ITSGNGASVTASDIEVIEGINSTAGNAGEATVSVV---AHLWYFFAISEC -295
             |||  |  |  ||| || | |   |  || |            || |||
MDLA_PENCA-  ITSPNNATVSTSDIKVIDGDVSFDGNTGTGLPLLTDFEAHIWYFVQVDAG -295

LIPASE3-  L--------L                                         -297
MDLA_PENCA-  KGPGLPFKRV                                         -305
```

Identity: 126 amino acids (42.42%)

The N-terminal of the mature lipase has been determined by N-terminal sequencing to be the serine residue No. 28 of the lipase 3 precursor (SEQ ID NO:9) as shown in Table 6.4 below. Hence the amino acids No. 1 to No. 27 is the signal sequence.

TABLE 6.4

Amino acid sequence of the precursor of lipase 3

```
             5           10          15          20          25          30
             |           |           |           |           |           |
  1  M F S G R F G V L L T A L A A L G A A A P A P L A V R S V S
 31  T S T L D E L Q L F A Q W S A A A Y C S N N I D S K D S N L
 61  T C T A N A C P S V E E A S T T M L L E F D L T N D F G G T
 91  A G F L A A D N T N K R L V V A F R G S S T I E N W I A N L
121  D F I L E D N D D L C T G C K V H T G F W K A W E S A A D E
151  L T S K I K S A M S T Y S G Y T L Y F T G H S L G G A L A T
181  L G A T V L R N D G Y S V E L Y T Y G C P R I G N Y A L A E
211  H I T S Q G S G A N F R V T H L N D I V P R V P P M D F G F
241  S Q P S P E Y W I T S G N G A S V T A S D I E V I E G I N S
271  T A G N A G E A T V S V V A H L W Y F F A I S E C L L
```

Number of residues: 297.

Residues 167–176 are recognised as a common motif for the serine lipases (PROSITE). The crystal structure for the *Rhizomucor miehei* serine lipase has been examined and the residues in the active site identified (Brady et al., Nature, 1990, 343:767–770; Derewanda et al., J. Mol. Biol., 1992, 227:818–839). The active site residues of R. miehei lipase have all been conserved in all the lipases and correspond to the following residues in lipase 3: serine 173, aspartic acid 228 and histidine 285.

Lipase 3 contains 7 cysteine residues. Four of these are conserved in the *P. camembertii* lipase where they form disulphide bonds (Isobe and Nokuhara, Gene, 1991, 103:61–67). This corresponds to disulphide bonds between residue 62–67 and 131–134. In addition, two cysteine residues are homologous to two C residues which forms an additional disulphide bond in Rhizopus and Rhizomucor lipases corresponding to residues 49–295.

Two putative N-glycosylation sites were found in lipase 3 in position 59 and 269. Neither of these are conserved in the other fungal lipases.

EXAMPLE 7

Transformation of *Aspergillus tubigensis* and overexpression of lipase 3 in *A. tubigensis*

The protocol for transformation was based on the teachings of Buxton et al. (Gene, 1985, 37:207–214), Daboussi et al (Curr. Genet., 1989, 15:453–456) and Punt and van den Hondel, (Meth. Enzym., 1992, 216:447–457).

A multicopy lipA strain was produced by transforming the pLIP4 plasmid into *Aspergillus tubigensis* strain 6M 179 using cotransformation with a hygromycin resistant marker plasmid.

A screening procedure used to visualise fungal lipase after ultrathin layer isoelectric focusing was adapted to screen *Aspergillus tubigensis* transformants grown on agar plates.

Screening of lipase producers on agar plates was done using 2% olive oil as the substrate for the enzyme (lipase) as well as the inducer for the lipase promoter. In addition, the plates contained a fluorescent dye, Rhodamine B. In the presence of olive oil, the transformants will be induced to secrete lipase. The lipase secreted into the agar plate will hydrolyse the olive oil causing the formation of orange fluorescent colonies that is visible upon UV radiation (350 nm). The appearance of fluorescent colonies was generally monitored after 24 hours of growth. After several days of growth, the lipase producing strains could be identified as orange fluorescent strains that are visible by eye. Under this plate screening condition, the untransformed strain gave no background fluorescence and appeared as opaque pink colonies.

Sixteen transformants that showed orange fluorescent halos were cultivated for 8 days in shake flasks containing 100 ml of minimal medium supplemented with 1% olive oil, 0.5% yeast extract and 0.2% casamino acids. The amount of lipase secreted was quantified by applying 10 $\mu$l of cell-free culture supernatant into holes punched in olive oil-Rhodamine B agar plates and incubating the plates overnight at 37° C. Five transformants with higher lipase production were found.

Figure 3:
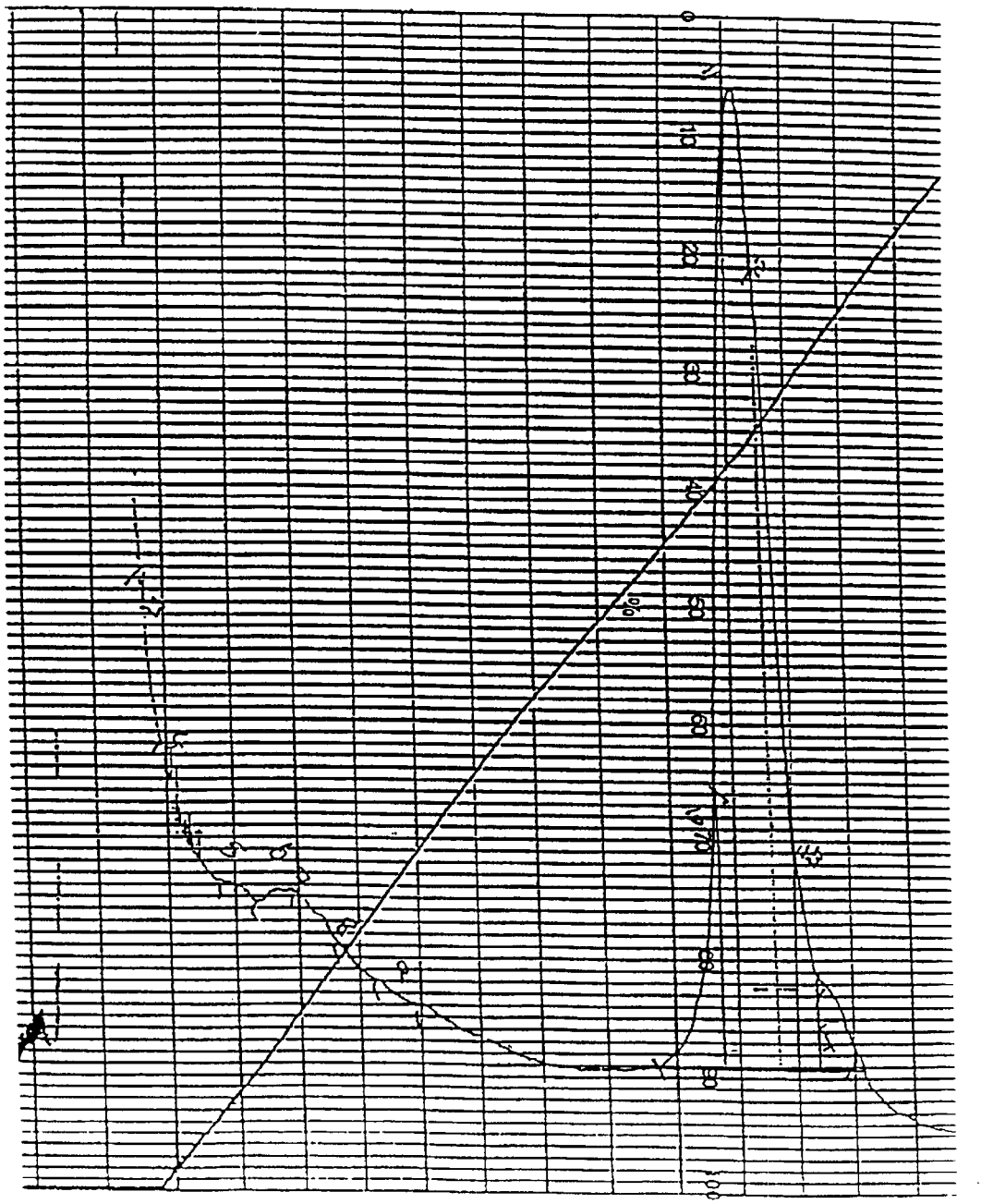
FIG. 3 shows a chromatogram of HIC fractionated culture supernatant of an *Aspergillus tubigensis* transformant with 62-fold increase of lipase 3.
Figure 4:
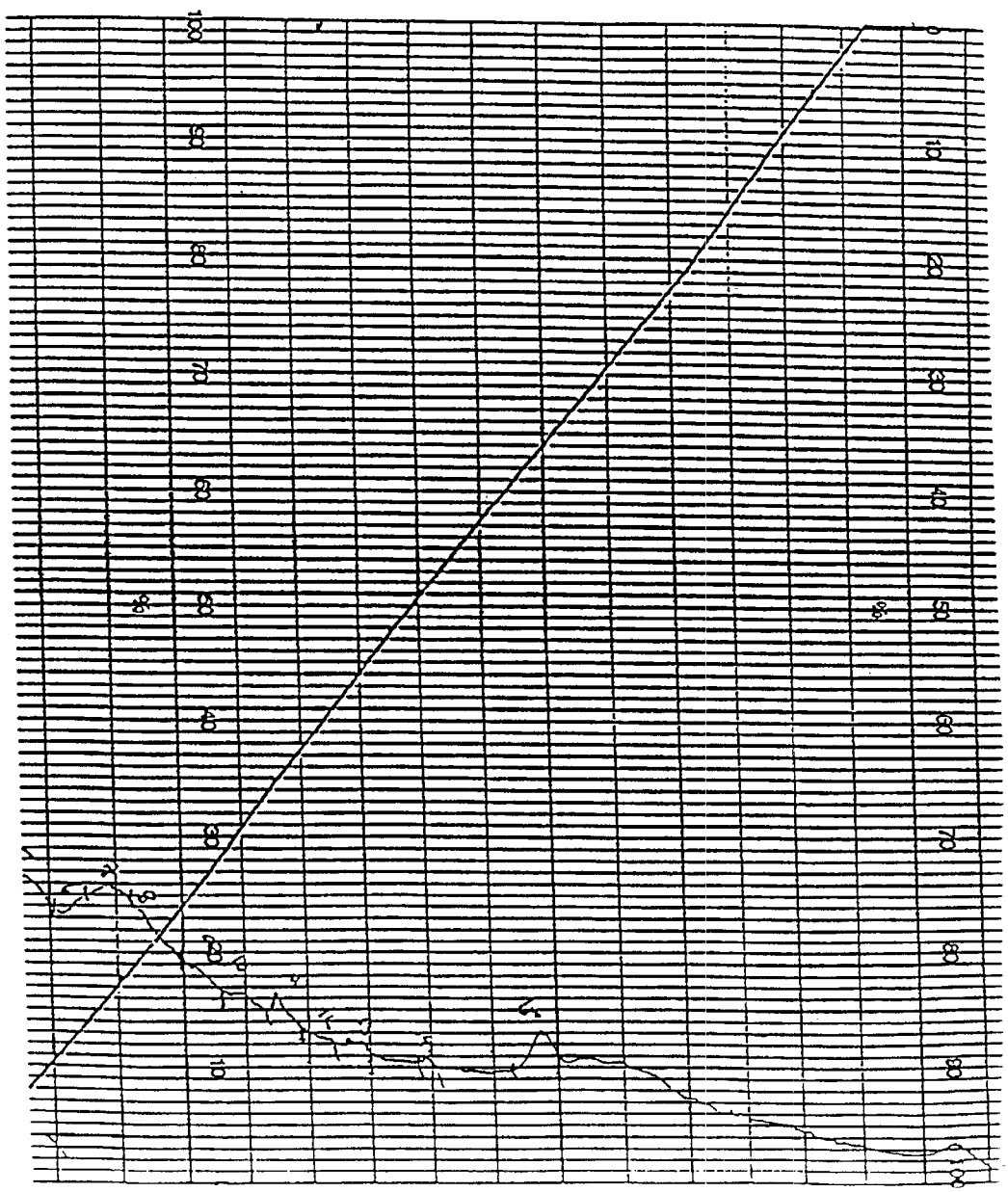
FIG. 4 shows a chromatogram of HIC fractionated culture supernatant of the untransformed *Aspergillus tubigensis* strain.

The cell-free culture supernatants from the five transformants were desalted using NAP 5 columns (Pharmacia) and equilibrated in 1M ammonium sulfate (50 mM sodium acetate, pH 5.5). The desalted culture supernatants were fractionated by hydrophobic interaction chromatography (HIC) on a Biogel Phenyl-5 PW column (Biorad). Elution was done by a descending salt gradient of 1M to 0 M ammonium sulfate (20 mM sodium acetate, pH 5.5). A single discrete protein peak was observed after fractionation. The area of the protein peaks were calculated among the different transformants and compared with the untransformed strain. The best transformant showed a 62-fold increase in the amount of lipase after HIC fractionation. A chromatogram of the HIC fractionated culture supernatant of this transformant is shown in FIG. 3 and a similar chromatogram for the untransformed strain is shown in FIG. 4.

The fraction containing the transformed lipase was freeze-dried. The transformed lipase was carboxymethylated and subjected to N-terminal amino acid sequencing of the first 15 amino acids and it was found that the sequence of the recombinant lipase was exactly the same as the native lipase indicating correct signal sequence cleavage.

The different lipase fractions collected after HIC were separated on a 12% Tris-Glycine SDS gel and silver staining revealed one protein band, confirming the homogeneity of the fractions. In addition, the crude extract showed a major lipase band as the only band that accumulated in the culture supernatant in very high amounts when the fungus was cultured in the olive oil-containing medium.

The recombinant lipase was analysed by matrix-assisted laser desorption ionisation (MALDI) by means of a time-of-flight (TOF) mass spectrometer as described hereinbefore. The molecular weight of the recombinant lipase was 32,237 Da.

Detection of N-linked oligosaccharides was achieved by digestion of the lipase with endo-$\beta$-N-acetyl-glucosamidase H from Streptomyces (Sigma). Digestion of recombinant lipase secreted into the growth medium altered the mobility of the band seen on SDS-PAGE which moved as a single band with a molecular mass of about 30 kDa.

Deglycosylated recombinant lipase generated by digestion with endoglycosidase and analysed directly by MALDI mass spectrometry gave a molecular weight of the polypeptide backbone of 29,325 Da.

C. BAKING EXPERIMENTS

EXAMPLE 8

Baking Experiments Using Lipase 3

8.1. Baking procedures and analytical methods (i) Baking procedure for Danish toast bread Flour (Danish reform flour) 2000 g, dry yeast 30 g, salt 30 g and water corresponding to 400 Brabender units+3%, was kneaded in a Hobart Mixer with hook for 2 min. at low speed and 10 min. at high speed. Dough temperature after kneading was 25° C. Resting time was 10 min. at 30° C. The dough was scaled 750 g per dough and rested again for 5 min at 33° C. and 85% RH. After moulding on a Glimik moulder, the dough were proofed in tins for 50 min at 33° C. and baked in a Wachtel oven for 40 min at 220° C. with steam injection for 16 sec. After cooling, the bread was scaled and the volume of the bread was measured by the rape seed displacement method. The specific volume is calculated by dividing the bread volume (ml) by the weight (g) of the bread.

The crumb was evaluated subjectively using a scale from 1 to 5 where 1=coarsely inhomogeneous and 5=nicely homogeneous.

Three breads baked in tins with lid were stored at 20° C. and used for firmness measurements and pore measurements by means of an Image Analyzer.

(ii) Baking procedure for Danish rolls

Flour (Danish reform) 1500 g, compressed yeast 90 g, sugar 24 g, salt 24 g and water corresponding to 400 Brabender units–2% were kneaded in a Hobart mixer with hook for 2 min. at low speed and 9 min at high speed. After kneading, the dough temperature was 26° C. The dough was scaled 1350 g. After resting for 10 min. at 30° C., the dough was moulded on a Fortuna moulder after which the dough was proofed for 45 min. at 34° C. and baked in a Bago oven for 18 min. at 220° C. with steam injection for 12 sec. After cooling, the rolls were scaled and the volume of the rolls was measured by the rape seed displacement method. Specific volume is calculated as described above.

(iii) Determination of pore homogeneity

The pore homogeneity of the bread was measured by means of an image analyzer composed of a standard CCD-video camera, a video digitiser and a personal computer with WinGrain software. For every bread, the results of pore diameter in mm and pore homogeneity were calculated as an average of measurements from 10 slices of bread. The pore homogeneity was expressed in % of pores that are larger than 0.5 times the average of pore diameter and smaller than 2 times the average diameter.

(iv) Determination of firmness

The firmness of bread, expressed as $N/dm^2$, was measured by means of an Instron UTM model 4301 connected to a personal computer. The conditions for measurement of bread firmness were:

| | |
|---|---|
| Load Cell | Max. 100 N |
| Piston diameter | 50 mm |
| Cross head speed | 200 mm/min |
| Compression | 25% |
| Thickness of bread slice | 11 mm |

The result was an average of measurements on 10 bread slices for evert bread.

(v) Determination of gluten index

Gluten index was measured by means of a Glutomatic 2200 from Perten Instruments (Sweden). Immediately after proofing, 15 g of dough was scaled and placed in the Glutomatic and washed with 500 ml 2% NaCl solution for 10 min. The washed dough was transferred to a Gluten Index Centrifuge 2015 and the two gluten fractions were scaled and the gluten index calculated according to the following equation:

Gluten index=(weight of gluten remaining on the sieve× 100)/total weight of gluten (vi) Extraction of lipids from dough 30 g of fully proofed dough was immediately frozen and freeze-dried. The freeze-dried dough was milled in a coffee mill and passed through a 235 $\mu$m screen. 4 g freeze-dried dough was scaled in a 50 ml centrifuge tube with screw lid and 20 ml water saturated n-butanol (WSB) was added. The centrifuge tube was placed in a water bath at a temperature of 100° C. for 10 min. after which the tubes were placed in a Rotamix and turned at 45 rpm for 20 min. at ambient temperature. The tubes were again placed in the water bath for 10 min. and turned on the Rotamix for another 30 min. at ambient temperature.

The tubes were centrifuged at 10,000×g for 5 min. 10 ml of the supernatant was pipetted into a vial and evaporated to dryness under nitrogen cover. This sample was used for HPLC analysis.

A similar sample was fractionated on a Bond Elut Si (Varian 1211–3036). The non-polar fraction was eluted with 10 ml cyclohexan:isopropanol:acetic acid (55:45:1) and evaporated to dryness. This sample was used for GLC analysis.

(vii) HPLC analysis

Column: LiChrospher 100 DIOL 5 $\mu$m (Merck art. 16152) 250×4 mm with a water jacket of a temperature of 50° C.

Mobile phases:

A: heptan:isopropanol:n-butanol:tetrahydrofuran:isooctan:water (64.5:17.5:7:5:5:1)

B: isopropanol:n-butanol:tetrahydrofuran:isooctan:water (73:7:5:5:10)

The mobile phases contained 1 mmol trifluoroacetic acid per 1 mobile phase and were adjusted to pH 6.6 with ammonia.

Pump: Waters 510 equipped with a gradient controller.

| | Gradient: | | |
|---|---|---|---|
| Flow (ml/min) | Time (min) | A (%) | B (%) |
| 1.0 | 0 | 100 | 0 |
| 1.0 | 25 | 0 | 100 |
| 1.0 | 30 | 0 | 100 |
| 1.0 | 35 | 100 | 0 |
| 1.0 | 40 | 100 | 0 |

Detector: CUNOW DDL21 (evaporative light-scattering); temperature 100° C.; voltage: 600 volt; air flow: 6.0 l/min.

Injector: Hewlett Packard 1050; injection volume: 50 $\mu$l.

The samples for analysis were dissolved in 5 ml chloroform:methanol (75:25), sonicated for 10 min and filtered through a 0.45 $\mu$m filter.

(viii) GLC analysis

Perkin Elmer 8420 Capillary Gas Chromatograph equipped with WCOT fused silica column 12.5 m×0.25 mm coated with 0.1 $\mu$m stationary phase of 5% phenyl-methyl-silicone (CP Sil 8 CB from Crompack).

Carrier: Helium

Injection: 1.5 $\mu$l with split

Detector: FID 385° C.

| Oven program: | 1 | 2 | 3 | 4 |
|---|---|---|---|---|
| Oven temperature, ° C. | 80 | 200 | 240 | 360 |
| Isothermal time, min | 2 | 0 | 0 | 10 |
| Temperature rate, ° C./min | 20 | 10 | 12 | — |

Sample preparation: 50 mg non-polar fraction of wheat lipids was dissolved in 12 ml heptane:pyridine (2:1) containing 2 mg/ml heptadecane as internal standard. 500 $\mu$l of the solution was transferred to a crimp vial and 100 $\mu$l N-methyl-N-trimethylsilyl-trifluoracetamide was added. The mixture was allowed to react for 15 min at 90° C.

Calculation: Response factors for mono-, di- and triglycerides and free fatty acids were determined from reference mixtures of these components. Based on these response factors, the glycerides and the free fatty acids were calculated in wheat lipids.

8.2. Baking experiments with lipase 3 in Danish toast bread

The effect of adding lipase 3 to a dough for making Danish toast bread was evaluated. The enzyme was added as a freeze-dried preparation on maltodextrin together with the other ingredients. The results of the baking tests are shown in Tables 8.1 to 8.4.

TABLE 8.1

| Lipase LUS/kg flour | 0 | 5,000 | 15,000 | 25,000 |
|---|---|---|---|---|
| Specific volume of bread | 4.43 | 4.43 | 4.22 | 4.37 |
| Firmness Day 1 | 35 | 33 | 32 | 30 |
| Firmness Day 7 | 90 | 90 | 85 | 73 |

TABLE 8.2

| Lipase LUS/kg flour | 0 | 5,000 | 15,000 | 25,000 |
|---|---|---|---|---|
| Average diameter of the crumb pore, mm | 2.96 | 2.33 | 2.47 | 2.65 |
| Homogeneity of crumb pore, % | 64.9 | 73.8 | 66.0 | 67.1 |
| Porosity, % | 85.9 | 84.7 | 85.5 | 85.1 |
| Gluten index, % | 42 | 45.5 | 55 | 65 |

TABLE 8.3

| Lipase LUS/kg flour | 0 | 5,000 | 15,000 | 25,000 |
|---|---|---|---|---|
| Fatty acids, % | 0.090 | 0.148 | 0.218 | 0.241 |
| Monoglycerides, % | 0.017 | 0.031 | 0.035 | 0.039 |
| Diglycerides, % | 0.020 | 0.036 | 0.040 | 0.045 |
| Triglycerides, % | 0.790 | 0.714 | 0.673 | 0.622 |

TABLE 8.4

| Lipase LUS/kg flour | 0 | 5,000 | 15,000 | 25,000 |
|---|---|---|---|---|
| Monogalactosyl diglyceride, % | 0.073 | 0.040 | 0.025 | 0.018 |
| Digalactosyl diglyceride, % | 0.244 | 0.220 | 0.182 | 0.127 |
| Digalactosyl monoglyceride, % | 0.008 | 0.022 | 0.044 | 0.054 |
| Phosphatidyl choline, % | 0.064 | 0.073 | 0.055 | 0.041 |
| Lysophosphatidyl choline, % | 0.164 | 0.182 | 0.171 | 0.165 |

By the addition of up to about 5,000 LUS/kg flour of the lipase no change in bread volume was observed, but at a higher dosage of lipase 3 there was a tendency to a small but not statistically significant decrease in volume (Table 8.1).

From the results in Table 8.2 it appears that lipase 3 improved the bread crumb homogeneity and that the average diameter of the crumb pores was reduced significantly. The gluten index also clearly correlated to the addition of lipase 3 as an indication of a more firm gluten caused by the modification of the wheat lipid components causing better dough stability and a more homogeneous bread pore structure. However, these modifications appeared to be optimal at the addition of 5,000 LUS/kg flour of lipase 3 whereas a higher dosage resulted in a too strong modification of the wheat gluten.

The results of the GLC and HPLC analyses (Table 8.3) clearly demonstrated that the triglycerides in the dough were hydrolysed. But more interestingly, there was also observed a modification of the glycolipids, monogalactosyl diglyceride and digalactosyl diglyceride. These components were converted to the more polar components monogalactosyl monoglyceride and digalactosyl monoglyceride. As digalactosyl monoglyceride is a more surface active component than digalactosyl diglyceride it is assumed that this component contributed to the observed improved crumb cell structure and homogeneity. It also appeared that phospholipids like phosphatidyl choline were only modified to a very small extent.

8.3. Baking experiments with lipase 3 in Danish rolls

The effect of adding lipase 3 to a dough for making Danish rolls was evaluated. The enzyme was added as a freeze-dried preparation on maltodextrin together with the other ingredients. The results of the baking tests are shown in Tables 8.5 to 8.7.

TABLE 8.5

| Lipase 3 LUS/kg flour | 0 | 10,000 | 20,000 | 30,000 |
|---|---|---|---|---|
| Specific volume of bread (45 min fermentation) | 6.86 | 7.04 | 6.35 | 6.36 |
| Specific volume of bread (65 min fermentation) | 8.30 | 8.59 | 8.23 | 8.04 |
| Subjective evaluation of crumb homogeneity | 3 | 5 | 4 | 4 |

TABLE 8.6

| Lipase 3 LUS/kg flour | 0 | 10,000 | 20,000 | 30,000 |
|---|---|---|---|---|
| Free fatty acids, % | 0.060 | 0.126 | 0.173 | 0.211 |
| Monoglycerides, % | 0.028 | 0.050 | 0.054 | 0.063 |

TABLE 8.6-continued

| Lipase 3 LUS/kg flour | 0 | 10,000 | 20,000 | 30,000 |
|---|---|---|---|---|
| Diglycerides, % | 0.103 | 0.095 | 0.110 | 0.104 |
| Triglycerides, % | 0.705 | 0.561 | 0.472 | 0.436 |

TABLE 8.7

| Lipase 3 LUS/kg flour | 0 | 5,000 | 15,000 | 25,000 |
|---|---|---|---|---|
| Digalactosyl diglyceride, % | 0.204 | 0.187 | 0.154 | 0.110 |
| Digalactosyl monoglyceride, % | 0.007 | 0.026 | 0.047 | 0.074 |
| Phosphatidyl choline, % | 0.077 | 0.078 | 0.077 | 0.063 |
| Lysophosphatidyl choline, % | 0.153 | 0.161 | 0.162 | 0.150 |

It is apparent from the results shown in Table 8.5 that the addition of lipase 3 does not significantly increase the volume of the rolls. Furthermore, lipase 3 was found to improve the homogeneity of the crumb.

The GLC and HPLC analyses of the wheat lipids, as shown in Tables 8.6 and 8.7, demonstrated the modification of these lipids.

EXAMPLE 9

Dough improving effect of glycerol oxidase and lipase

The effect of glycerol oxidase and lipase (separately or in combination) on dough strength was studied in a dough prepared according to the AACC Method 54-10. The dough was subjected to extensiograph measurements (Barbender Extensiograph EXEK/6) also according to AACC Method 54-10 with and with out the addition of glycerol oxidase from *Aspergillus japonicus* combined with lipase from *Aspergillus oryzae* (GRIN-DAMYL™ EXEL 16, Bakery Enzyme, Danisco Ingredients). The dough with out addition of enzymes served as a control.

The principle of the above method is that the dough after forming is subjected to a load-extension test after resting at 30° C. for 45, 90 and 135 minutes, respectively, using an extensigraph capable of recording a load-extension curve (extensigram) which is an indication of the doughs resistance to physical deformation when stretched. From this curve, the resistance to extension, B (height of curve) and the extensibility, C (total length of curve) can be calculated. The B/C ratio (D) is an indication of the baking strength of the flour dough. The results of the experiment are summarized in Table 9.1 below.

TABLE 9.1

Extensigraph measurements of dough supplemented with glycerol oxidase and lipase

| Sample (per kg flour) | Resting time (min) | B-value | C-value | D = B/C |
|---|---|---|---|---|
| Control | 45 | 220 | 192 | 1.15 |
| 500 LUS lipase | 45 | 225 | 190 | 1.18 |
| 1000 U glycerol | 45 | 300 | 195 | 1.54 |

TABLE 9.1-continued

Extensigraph measurements of dough supplemented
with glycerol oxidase and lipase

| Sample (per kg flour) | Resting time (min) | B-value | C-value | D = B/C |
|---|---|---|---|---|
| oxidase | | | | |
| 500 LUS lipase + 1000 U Glycerol oxidase | 45 | 350 | 198 | 1.77 |
| Control | 90 | 240 | 196 | 1.22 |
| 500 LUS lipase | 90 | 245 | 195 | 1.16 |
| 1000 U Glycerol oxidase | 90 | 330 | 190 | 1.74 |
| 500 LUS lipase + 1000 U Glycerol oxidase | 90 | 380 | 192 | 1.98 |
| Control | 135 | 260 | 188 | 1.38 |
| 500 LUS lipase | 135 | 265 | 190 | 1.39 |
| 1000 U Glycerol oxidase | 135 | 380 | 188 | 2.02 |
| 500 LUS lipase + 1000 U Glycerol oxidase | 135 | 410 | 190 | 2.15 |

When the results from the above experiments are compared with regard to the differences between the control dough and the glycerol oxidase supplemented dough it appears that glycerol oxidase clearly has a strengthening effect. The B/C ratio was increased by 34%, 43% and 46% after 45, 90 and 135 minutes of resting time respectively.

The addition of lipase only did not have any effect on the B/C ratio.

However, when supplementing the dough with a combination of glycerol oxidase and lipase, a further increase in the B/C ratio was seen as compared to bread prepared from dough supplemented with glycerol oxidase only. The B/C ratio was increased by 54%, 62% and 56% after 45, 90 and 135 minutes respectively. This clearly indicates that the combined use of these two enzymes in the preparation of bread products has an enhancing effect on the baking strength.

EXAMPLE 10

Improvement of the specific volume of bread prepared from dough supplemented with glycerol oxidase and lipase The effect of using glycerol oxidase and lipase (separately or in combination) on the specific bread volume and the crumb homogeneity was tested in a baking procedure for Danish rolls with a dough prepared as described in example 8. Glycerol oxidase from *Aspergillus japonicus* and lipase 3 from *Aspergillus tubigensis* was added to the dough in different amounts. Dough without the addition of enzymes served as control. The fully proofed dough was baked at 220° C. for 18 minutes with 12 seconds steam in a Bago-oven. After cooling the rolls were weighed and the volume of the rolls were measured by the rape seed displacement method. The specific bread volume was determined as the volume of the bread (ml) divided by the weight of the bread (g). The crumb homogeneity was evaluated subjectively on a scale from 1 to 7, where 1=course inhomogeneous and 7=nice homogeneous. The results from this experiment are summarized in Table 10.1 below.

TABLE 10.1

Specific volume and crumb homogeneity in bread
supplemented with lipase and glycerol

| Sample (per kg flour) | Specific volume (ml/g) | Crumb homogeneity |
|---|---|---|
| Control | 5.45 | 1 |
| 1,000 U glycerol oxidase | 6.75 | 2 |
| 10,000 LUS lipase | 5.65 | 4 |
| 10,000 LUS lipase + 1,000 U glycerol oxidase | 7.25 | 7 |

As can be seen in the above Tabel 10.1, the use of glycerol oxidase in the preparing of bread, significantly increased the bread volume (24%) as compared to bread prepared from a similar dough not supplemented with this enzyme. Addition of glycerol oxidase did not improve the crumb homogeneity significantly.

The use of lipase in the preparing of bread did not increase the specific volume of the bread, however a highly increased pore homogeneity was observed.

The combined use of glycerol oxidase and lipase increased the specific volume of the bread with 33% as compared to bread prepared from a similar dough not supplemented with any of the two enzymes.

In addition, the crumb homogeneity was highly improved by the combined use of lipase and glycerol oxidase as compared to the control bread and the breads prepared from dough supplemented with lipase and glycerol oxidase respectively.

This clearly indicates that the combination of lipase and glycerol oxidase in the preparation of bread has a synergistic effect and significantly enhances the shape and appearance of the finished bread product.

EXAMPLE 11

Hydrolysis of triglycerides and formation of glycerol in dough supplemented with lipase In order to study the hydrolysis of triglycerides and the formation of glycerol in a proofed dough supplemented with lipase, a dough for Danish rolls was prepared in the same manner as described in example 8. Different amounts of lipase (GRINDAMYL™ EXEL 16) was added to the dough, and the total lipid from the fully proofed dough was extracted and analyzed by gas chromatography as described above.

TABLE 11.1

Triglycerides and glycerol in a dough as a function of lipase addition

| Lipase addition (GRINDAMYL ™ EXEL 16) (LUS per kg flour) | Glycerol (%) | Triglycerides (%) |
|---|---|---|
| 0 | 2.2 | 7.88 |
| 500 | 2.2 | 6.22 |
| 1,250 | 2.4 | 5.99 |
| 2,500 | 2.8 | 5.37 |
| 3,750 | 2.9 | 5.47 |
| 5,000 | 3.0 | 5.55 |
| 7,500 | 3.1 | 5.03 |
| 10,000 | 3.0 | 4.39 |

From the above experiment it is clear that the addition of lipase to a dough has a hydrolyzing effect on the triglycerides present in the dough, which is seen as a decrease in the triglyceride content as function of the increased lipase addition. The resulting level of glycerol increases as a function of the lipase addition. These results suggests, that the improvement of the B/C ratio and the specific bread volume in bread prepared from dough supplemented with both glycerol oxidase and lipase, as was seen in example 9 and 10, could be due to that lipase addition to a dough is generating glycerol which further can act as substrate for glycerol oxidase.

What is claimed is:

1. A method of altering the rheological properties of a flour dough and the quality of the finished product made from the dough, comprising adding to the dough a glycerol oxidase, which does not require a co-factor to oxidize glycerol, and a lipase, wherein the combined effect of the glycerol oxidase and the lipase on said rheological properties is synergistic.

2. A method according to claim 1 wherein the amount of the glycerol oxidase added is in the range of 10 to 10,000 units per kg flour.

3. A method according to claim 2 wherein the glycerol oxidase is derived from an organism selected from the group consisting of a bacterial species, a fungal species, a yeast species, an animal cell and a plant cell.

4. A method according to claim 3 wherein the fungal species comprises an Aspergillus species, a Neurospora species or a Penicillium species.

5. A method according to claim 4 wherein the Aspergillus species comprises *A. japonicus, A. oryzae, A. parasiticus*, or *A. flavus*.

6. A method according to claim 4 wherein the Neurospora species comprises *N. crassa, N. sitophila*, or *N. tetrasperma*.

7. A method according to claim 4 wherein the Penicillium species comprises *P. nigricans, P. funiculosum* or *P. janthinellum*.

8. A method according to claim 1 wherein the amount of the lipase added is in the range of 10 to 100,000 LUS per kg of flour.

9. A method according to claim 1 wherein the lipase is derived from an organism comprising a bacterial species, a fungal species, a yeast species, an animal cell or a plant cell.

10. A method according to claim 9 wherein the lipase is derived from an Aspergillus species.

11. A method according to claim 10 wherein the Aspergillus species comprises *A. tubigensis, A. oryzae* or *A. niger*.

12. A method according to claim 1 wherein the lipase comprises at least one of the following amino acid sequences: SEQ ID NO:1, SEQ ID NO:2, SEQ ID NO:3 or SEQ ID NO:9.

13. A method according to claim 1 wherein the alteration of the rheological properties includes an increase in the resistance to extension of the dough, in terms of the ratio between resistance to extension (height of curve, B) and the extensibility (length of curve, C), expressed as the B/C ratio, as measured by the AACC method 54-10, relative to that of an otherwise similar dough not containing glycerol oxidase and lipase.

14. A method according to claim 13 wherein the resistance to extension of the dough is increased by at least 10%.

15. A method according to claim 13 wherein the resistance to extension of the dough is increased by at least 25%.

16. A method according to claim 1 wherein the alteration of the quality of the finished product made from the dough includes an increase in the pore homogeneity of the crumb of the bread made from the dough by at least 5%, relative to a bread which is made from a bread dough without addition of the glycerol oxidase and lipase.

17. A method according to claim 1 wherein the alteration of the rheological properties includes an increase in the specific volume of the finished product relative to an otherwise similar product prepared from a dough not containing lipase and glycerol oxidase.

18. A method according to claim 17 wherein the specific volume is increased by at least 10%.

19. A method according to claim 17 wherein the specific volume is increased by at least 30%.

20. A method according to claim 1 wherein the finished product comprises at least one of a bread product, a noodle product or an alimentary paste product.

21. A method according to claim 1 wherein at least one further enzyme is added to the dough ingredients, dough additives or the dough.

22. A method according to claim 21 wherein the further enzyme comprises a cellulase, a hemicellulase, a starch degrading enzyme, an oxidoreductase, or a protease.

23. A flour dough altering composition which is a pre-mixture containing all of the dry ingredients and additives for a flour dough, and further comprising a glycerol oxidase, which does not require a co-factor to oxidize glycerol, and a lipase and at least one further dough additive comprising at least one of a monoglyceride, a diacetyl tartaric acid ester of mono- or diglycerides of fatty acids, a starch degrading enzyme, a cellulose or hemicellulose degrading enzyme, a protease, a non-specific oxidizing agent, a flavoring agent, a lactic acid bacterial culture, a vitamin, a mineral, an alginate, a carrageenan, a pectin, a vegetable gum, or a dietary fiber substance, which composition, when it is added to a flour dough, results in a synergistic effect of the glycerol oxidase and the lipase on the rheological properties of the flour dough and the quality of the finished product made from the flour dough.

24. A flour dough altering composition according to claim 23, wherein the synergistic effect on the rheological properties of the flour dough and the quality of the finished product includes: i) increased resistance to extension of the dough, ii) increased pore homogeneity of the crumb of the bread made from the dough or, iii) increased specific volume of the finished product.

25. A composition according to claim 23 wherein the further dough additive additionally comprises a substrate for glycerol oxidase, an emulsifying agent or a hydrocolloid.

26. A composition according to claim 25 wherein the hydrocolloid comprises an alginate, a carrageenan, a pectin or a vegetable gum.

27. A method of preparing a finished product, made from a flour dough, which comprises at least one of a baked product, a noodle product or an alimentary paste product, comprising adding to the flour dough a pre-mixture which includes about 10 to 10,000 units per kg flour of a glycerol oxidase, which does not require a co-factor to oxidize glycerol, and about 10 to 100,000 LUS per kg flour of lipase, which pre-mixture, when it is added to the flour dough, results in a synergistic effect of the glycerol oxidase and the lipase on the rheological properties of the flour dough and the quality of the finished product made from the flour dough.

28. A method according to claim 13 wherein the resistance to extension of the dough is increased by at least 50%.

29. A method according to claim 13 wherein the resistance to extension of the dough is increased by at least 75%.

30. The composition of claim 23 wherein the amount of glycerol oxidase is in the range of 10 to 5,000 units per kg flour.

31. The composition of claim 23 wherein the amount of lipase is in the range of 10 to 20,000 LUS per kg flour.

* * * * *

SEQUENCE LISTING

```
<160> NUMBER OF SEQ ID NOS: 18

<210> SEQ ID NO 1
<211> LENGTH: 25
<212> TYPE: PRT
<213> ORGANISM: Aspergillus tubingensis
<220> FEATURE:
<221> NAME/KEY: UNSURE
<222> LOCATION: (22)..(22)
<223> OTHER INFORMATION: UNSURE

<400> SEQUENCE: 1

Ser Val Ser Thr Ser Thr Leu Asp Glu Leu Gln Leu Phe Ala Gln Trp
1               5                   10                  15

Ser Ala Ala Ala Tyr Xaa Ser Asn Asn
            20                  25

<210> SEQ ID NO 2
<211> LENGTH: 7
<212> TYPE: PRT
<213> ORGANISM: Aspergillus tubingensis

<400> SEQUENCE: 2

Val His Thr Gly Phe Trp Lys
1               5

<210> SEQ ID NO 3
<211> LENGTH: 14
<212> TYPE: PRT
<213> ORGANISM: Aspergillus tubingensis

<400> SEQUENCE: 3

Ala Trp Glu Ser Ala Ala Asp Glu Leu Thr Ser Lys Ile Lys
1               5                   10

<210> SEQ ID NO 4
<211> LENGTH: 20
<212> TYPE: DNA
<213> ORGANISM: Artificial
<220> FEATURE:
<223> OTHER INFORMATION: PCR primer
<221> NAME/KEY: Unsure
<222> LOCATION: (9)..(9)
<223> OTHER INFORMATION: Unsure
<221> NAME/KEY: Unsure
<222> LOCATION: (12)..(12)
<223> OTHER INFORMATION: Unsure
<221> NAME/KEY: Unsure
<222> LOCATION: (18)..(18)
<223> OTHER INFORMATION: Unsure

<400> SEQUENCE: 4
ttccaraanc cngtrtgnac                                              20

<210> SEQ ID NO 5
<211> LENGTH: 18
<212> TYPE: DNA
<213> ORGANISM: Artificial
<220> FEATURE:
<223> OTHER INFORMATION: PCR primer
```

```
<221> NAME/KEY: Unsure
<222> LOCATION: (6)..(6)
<223> OTHER INFORMATION: Unsure
<221> NAME/KEY: Unsure
<222> LOCATION: (12)..(12)
<223> OTHER INFORMATION: Unsure

<400> SEQUENCE: 5
carytnttyg cncartgg                                                   18

<210> SEQ ID NO 6
<211> LENGTH: 17
<212> TYPE: DNA
<213> ORGANISM: Artificial
<220> FEATURE:
<223> OTHER INFORMATION: PCR primer

<400> SEQUENCE: 6
gcvgchswyt cccavgc                                                    17

<210> SEQ ID NO 7
<211> LENGTH: 317
<212> TYPE: DNA
<213> ORGANISM: Aspergillus tubingensis

<400> SEQUENCE: 7
cagttgttcg cgcaatggtc tgccgcagct tattgctcga ataatatcga ctcgaaagav     60
tccaacttga catgcacggc caacgcctgt ccatcagtcg aggaggccag taccacgatg    120
ctgctggagt tcgacctgta tgtcactcag atcgcagaca tagagcacag ctaattgaac    180
aggacgaacg acttttggag gcacagccgg tttcctggcc gcggacaaca ccaacaagcg    240
gctcgtggtc gccttccggg gaagcagcac gattgagaac tggattgcta atcytgactt    300
catcctggra gataacg                                                  317

<210> SEQ ID NO 8
<211> LENGTH: 1045
<212> TYPE: DNA
<213> ORGANISM: Aspergillus tubingensis

<400> SEQUENCE: 8
atgttctctg gacggtttgg agtgcttttg acagcgcttg ctgcgctggg tgctgccgcg     60
ccggcaccgc ttgctgtgcg gagtaggtgt gcccgatgtg agatggttgg atagcactga    120
tgaagggtga ataggtgtct cgacttccac gttggatgag ttgcaattgt tcgcgcaatg    180
gtctgccgca gcttattgct cgaataatat cgactcgaaa gactccaact tgacatgcac    240
ggccaacgcc tgtccatcag tcgaggaggc cagtaccacg atgctgctgg agttcgacct    300
gtatgtcact cagatcgcag acatagagca gctaatttt gaacaggacg aacgactttg    360
gaggcacagc cggtttcctg gccgcggaca acaccaacaa gcggctcgtg gtcgccttcc    420
ggggaagcag cacgattgag aactggattg ctaatcttga cttcatcctg gaagataacg    480
acgacctctg caccggctgc aaggtccata ctggtttctg gaaggcatgg gagtccgctg    540
ccgacgaact gacgagcaag atcaagtctg cgatgagcac gtattcgggc tataccctat    600
acttcaccgg gcacagtttg gcggcgcat tggctacgct gggagcgaca gttctgcgaa    660
atgacggata tagcgttgag ctggtgagtc cttcacaaag gtgatggagc gacaatcggg    720
aacagacagt caatagtaca cctatggatg tcctcgaatc ggaaactatg cgctggctga    780
gcatatcacc agtcagggat ctggggccaa cttccgtgtt acacacttga acgacatcgt    840
```

```
cccccgggtg ccacccatgg actttggatt cagtcagcca agtccggaat actggatcac    900
cagtggcaat ggagccagtg tcacggcgtc ggatatcgaa gtcatcgagg gaatcaattc    960
aacggcggga aatgcaggcg aagcaacggt gagcgttgtg ctcacttgtg gtactttttt   1020
tgcgatttcc gagtgcctgc tataa                                         1045
```

<210> SEQ ID NO 9
<211> LENGTH: 297
<212> TYPE: PRT
<213> ORGANISM: Aspergillus tubingensis

<400> SEQUENCE: 9

```
Met Phe Ser Gly Arg Phe Gly Val Leu Leu Thr Ala Leu Ala Ala Leu
1               5                   10                  15

Gly Ala Ala Ala Pro Ala Pro Leu Ala Val Arg Ser Val Ser Thr Ser
                20                  25                  30

Thr Leu Asp Glu Leu Gln Leu Phe Ala Gln Trp Ser Ala Ala Ala Tyr
            35                  40                  45

Cys Ser Asn Asn Ile Asp Ser Lys Asp Ser Asn Leu Thr Cys Thr Ala
        50                  55                  60

Asn Ala Cys Pro Ser Val Glu Glu Ala Ser Thr Thr Met Leu Leu Glu
65                  70                  75                  80

Phe Asp Leu Thr Asn Asp Phe Gly Gly Thr Ala Gly Phe Leu Ala Ala
                85                  90                  95

Asp Asn Thr Asn Lys Arg Leu Val Val Ala Phe Arg Gly Ser Ser Thr
            100                 105                 110

Ile Glu Asn Trp Ile Ala Asn Leu Asp Phe Ile Leu Glu Asp Asn Asp
        115                 120                 125

Asp Leu Cys Thr Gly Cys Lys Val His Thr Gly Phe Trp Lys Ala Trp
    130                 135                 140

Glu Ser Ala Ala Asp Glu Leu Thr Ser Lys Ile Lys Ser Ala Met Ser
145                 150                 155                 160

Thr Tyr Ser Gly Tyr Thr Leu Tyr Phe Thr Gly His Ser Leu Gly Gly
                165                 170                 175

Ala Leu Ala Thr Leu Gly Ala Thr Val Leu Arg Asn Asp Gly Tyr Ser
            180                 185                 190

Val Glu Leu Tyr Thr Tyr Gly Cys Pro Arg Ile Gly Asn Tyr Ala Leu
        195                 200                 205

Ala Glu His Ile Thr Ser Gln Gly Ser Gly Ala Asn Phe Arg Val Thr
    210                 215                 220

His Leu Asn Asp Ile Val Pro Arg Val Pro Pro Met Asp Phe Gly Phe
225                 230                 235                 240

Ser Gln Pro Ser Pro Glu Tyr Trp Ile Thr Ser Gly Asn Gly Ala Ser
                245                 250                 255

Val Thr Ala Ser Asp Ile Glu Val Ile Glu Gly Ile Asn Ser Thr Ala
            260                 265                 270

Gly Asn Ala Gly Glu Ala Thr Val Ser Val Val Ala His Leu Trp Tyr
        275                 280                 285

Phe Phe Ala Ile Ser Glu Cys Leu Leu
    290                 295
```

<210> SEQ ID NO 10
<211> LENGTH: 392
<212> TYPE: PRT
<213> ORGANISM: Rhizopus delamar

```
<400> SEQUENCE: 10

Met Val Ser Phe Ile Ser Ile Ser Gln Gly Val Ser Leu Cys Leu Leu
1               5                  10                  15

Val Ser Ser Met Met Leu Gly Ser Ser Ala Val Pro Val Ser Gly Lys
            20                  25                  30

Ser Gly Ser Ser Asn Thr Ala Val Ser Ala Ser Asp Asn Ala Ala Leu
        35                  40                  45

Pro Pro Leu Ile Ser Ser Arg Cys Ala Pro Pro Ser Asn Lys Gly Ser
    50                  55                  60

Lys Ser Asp Leu Gln Ala Glu Pro Tyr Asn Met Gln Lys Asn Thr Glu
65                  70                  75                  80

Trp Tyr Glu Ser His Gly Gly Asn Leu Thr Ser Ile Gly Lys Arg Asp
                85                  90                  95

Asp Asn Leu Val Gly Gly Met Thr Leu Asp Leu Pro Ser Asp Ala Pro
            100                 105                 110

Pro Ile Ser Leu Ser Ser Thr Asn Ser Ala Ser Asp Gly Gly Lys
        115                 120                 125

Val Val Ala Ala Thr Thr Ala Gln Ile Gln Glu Phe Thr Lys Tyr Ala
    130                 135                 140

Gly Ile Ala Ala Thr Ala Tyr Cys Arg Ser Val Val Pro Gly Asn Lys
145                 150                 155                 160

Trp Asp Cys Val Gln Cys Gln Lys Trp Val Pro Asp Gly Lys Ile Ile
                165                 170                 175

Thr Thr Phe Thr Ser Leu Leu Ser Asp Thr Asn Gly Tyr Val Leu Arg
            180                 185                 190

Ser Asp Lys Gln Lys Thr Ile Tyr Leu Val Phe Arg Gly Thr Asn Ser
        195                 200                 205

Phe Arg Ser Ala Ile Thr Asp Ile Val Phe Asn Phe Ser Asp Tyr Lys
    210                 215                 220

Pro Val Lys Gly Ala Lys Val His Ala Gly Phe Leu Ser Ser Tyr Glu
225                 230                 235                 240

Gln Val Val Asn Asp Tyr Phe Pro Val Val Gln Glu Gln Leu Thr Ala
                245                 250                 255

His Pro Thr Tyr Lys Val Ile Val Thr Gly His Ser Leu Gly Gly Ala
            260                 265                 270

Gln Ala Leu Leu Ala Gly Met Asp Leu Tyr Gln Arg Glu Pro Arg Leu
        275                 280                 285

Ser Pro Lys Asn Leu Ser Ile Phe Thr Val Gly Gly Pro Arg Val Gly
    290                 295                 300

Asn Pro Thr Phe Ala Tyr Tyr Val Glu Ser Thr Gly Ile Pro Phe Gln
305                 310                 315                 320

Arg Thr Val His Lys Arg Asp Ile Val Pro His Val Pro Pro Gln Ser
                325                 330                 335

Phe Gly Phe Leu His Pro Gly Val Glu Ser Trp Ile Lys Ser Gly Thr
            340                 345                 350

Ser Asn Val Gln Ile Cys Thr Ser Glu Ile Glu Thr Lys Asp Cys Ser
        355                 360                 365

Asn Ser Ile Val Pro Phe Thr Ser Ile Leu Asp His Leu Ser Tyr Phe
    370                 375                 380

Asp Ile Asn Glu Gly Ser Cys Leu
385                 390

<210> SEQ ID NO 11
```

```
<211> LENGTH: 363
<212> TYPE: PRT
<213> ORGANISM: Rhizomucor miehei

<400> SEQUENCE: 11

Met Val Leu Lys Gln Arg Ala Asn Tyr Leu Gly Phe Leu Ile Val Phe
1               5                   10                  15

Phe Thr Ala Phe Leu Val Glu Ala Val Pro Ile Lys Arg Gln Ser Asn
            20                  25                  30

Ser Thr Val Asp Ser Leu Pro Pro Leu Ile Pro Ser Arg Thr Ser Ala
        35                  40                  45

Pro Ser Ser Ser Pro Ser Thr Thr Asp Pro Glu Ala Pro Ala Met Ser
    50                  55                  60

Arg Asn Gly Pro Leu Pro Ser Asp Val Glu Thr Lys Tyr Gly Met Ala
65                  70                  75                  80

Leu Asn Ala Thr Ser Tyr Pro Asp Ser Val Val Gln Ala Met Ser Ile
                85                  90                  95

Asp Gly Gly Ile Arg Ala Ala Thr Ser Gln Glu Ile Asn Glu Leu Thr
            100                 105                 110

Tyr Tyr Thr Thr Leu Ser Ala Asn Ser Tyr Cys Arg Thr Val Ile Pro
        115                 120                 125

Gly Ala Thr Trp Asp Cys Ile His Cys Asp Ala Thr Glu Asp Leu Lys
    130                 135                 140

Ile Ile Lys Thr Trp Ser Thr Leu Ile Tyr Asp Thr Asn Ala Met Val
145                 150                 155                 160

Ala Arg Gly Asp Ser Glu Lys Thr Ile Tyr Ile Val Phe Arg Gly Ser
                165                 170                 175

Ser Ser Ile Arg Asn Trp Ile Ala Asp Leu Thr Phe Val Pro Val Ser
            180                 185                 190

Tyr Pro Pro Val Ser Gly Thr Lys Val His Lys Gly Phe Leu Asp Ser
        195                 200                 205

Tyr Gly Glu Val Gln Asn Glu Leu Val Ala Thr Val Leu Asp Gln Phe
    210                 215                 220

Lys Gln Tyr Pro Ser Tyr Lys Val Ala Val Thr Gly His Ser Leu Gly
225                 230                 235                 240

Gly Ala Thr Ala Leu Leu Cys Ala Leu Asp Leu Tyr Gln Arg Glu Glu
                245                 250                 255

Gly Leu Ser Ser Ser Asn Leu Phe Leu Tyr Thr Gln Gly Gln Pro Arg
            260                 265                 270

Val Gly Asp Pro Ala Phe Ala Asn Tyr Val Val Ser Thr Gly Ile Pro
        275                 280                 285

Tyr Arg Arg Thr Val Asn Glu Arg Asp Ile Val Pro His Leu Pro Pro
    290                 295                 300

Ala Ala Phe Gly Phe Leu His Ala Gly Glu Glu Tyr Trp Ile Thr Asp
305                 310                 315                 320

Asn Ser Pro Glu Thr Val Gln Val Cys Thr Ser Asp Leu Glu Thr Ser
                325                 330                 335

Asp Cys Ser Asn Ser Ile Val Pro Phe Thr Ser Val Leu Asp His Leu
            340                 345                 350

Ser Tyr Phe Gly Ile Asn Thr Gly Leu Cys Thr
        355                 360

<210> SEQ ID NO 12
<211> LENGTH: 305
<212> TYPE: PRT
```

<213> ORGANISM: Penicillium camemberti

<400> SEQUENCE: 12

| | | | | | | | | | | | | | | | |
|---|---|---|---|---|---|---|---|---|---|---|---|---|---|---|---|
| Met | Arg | Leu | Ser | Phe | Phe | Thr | Ala | Leu | Ser | Ala | Val | Ala | Ser | Leu | Gly |
| 1 | | | | 5 | | | | | 10 | | | | | 15 | |
| Tyr | Ala | Leu | Pro | Gly | Lys | Leu | Gln | Ser | Arg | Asp | Val | Ser | Thr | Ser | Glu |
| | | | 20 | | | | | 25 | | | | | 30 | | |
| Leu | Asp | Gln | Phe | Glu | Phe | Trp | Val | Gln | Tyr | Ala | Ala | Ala | Ser | Tyr | Tyr |
| | | | 35 | | | | 40 | | | | | 45 | | | |
| Glu | Ala | Asp | Tyr | Thr | Ala | Gln | Val | Gly | Asp | Lys | Leu | Ser | Cys | Ser | Lys |
| | 50 | | | | | 55 | | | | | 60 | | | | |
| Gly | Asn | Cys | Pro | Glu | Val | Glu | Ala | Thr | Gly | Ala | Thr | Val | Ser | Tyr | Asp |
| 65 | | | | 70 | | | | | 75 | | | | | 80 | |
| Phe | Ser | Asp | Ser | Thr | Ile | Thr | Asp | Thr | Ala | Gly | Tyr | Ile | Ala | Val | Asp |
| | | | | 85 | | | | | 90 | | | | | 95 | |
| His | Thr | Asn | Ser | Ala | Val | Val | Leu | Ala | Phe | Arg | Gly | Ser | Tyr | Ser | Val |
| | | | 100 | | | | | 105 | | | | | 110 | | |
| Arg | Asn | Trp | Val | Ala | Asp | Ala | Thr | Phe | Val | His | Thr | Asn | Pro | Gly | Leu |
| | | | 115 | | | | | 120 | | | | | 125 | | |
| Cys | Asp | Gly | Cys | Leu | Ala | Glu | Leu | Gly | Phe | Trp | Ser | Ser | Trp | Lys | Leu |
| | 130 | | | | | 135 | | | | | 140 | | | | |
| Val | Arg | Asp | Asp | Ile | Ile | Lys | Glu | Leu | Lys | Glu | Val | Val | Ala | Gln | Asn |
| 145 | | | | | | 150 | | | | | 155 | | | | 160 |
| Pro | Asn | Tyr | Glu | Leu | Val | Val | Val | Gly | His | Ser | Leu | Gly | Ala | Ala | Val |
| | | | | 165 | | | | | 170 | | | | | 175 | |
| Ala | Thr | Leu | Ala | Ala | Thr | Asp | Leu | Arg | Gly | Lys | Gly | Tyr | Pro | Ser | Ala |
| | | | 180 | | | | | 185 | | | | | 190 | | |
| Lys | Leu | Tyr | Ala | Tyr | Ala | Ser | Pro | Arg | Val | Gly | Asn | Ala | Ala | Leu | Ala |
| | | | 195 | | | | | 200 | | | | | 205 | | |
| Lys | Tyr | Ile | Thr | Ala | Gln | Gly | Asn | Asn | Phe | Arg | Phe | Thr | His | Thr | Asn |
| | 210 | | | | | 215 | | | | | 220 | | | | |
| Asp | Pro | Val | Pro | Lys | Leu | Pro | Leu | Leu | Ser | Met | Gly | Tyr | Val | His | Val |
| 225 | | | | | | 230 | | | | | 235 | | | | 240 |
| Ser | Pro | Glu | Tyr | Trp | Ile | Thr | Ser | Pro | Asn | Asn | Ala | Thr | Val | Ser | Thr |
| | | | | 245 | | | | | 250 | | | | | 255 | |
| Ser | Asp | Ile | Lys | Val | Ile | Asp | Gly | Asp | Val | Ser | Phe | Asp | Gly | Asn | Thr |
| | | | 260 | | | | | 265 | | | | | 270 | | |
| Gly | Thr | Gly | Leu | Pro | Leu | Leu | Thr | Asp | Phe | Glu | Ala | His | Ile | Trp | Tyr |
| | | | 275 | | | | | 280 | | | | | 285 | | |
| Phe | Val | Gln | Val | Asp | Ala | Gly | Lys | Gly | Pro | Gly | Leu | Pro | Phe | Lys | Arg |
| | 290 | | | | | 295 | | | | | 300 | | | | |
| Val | | | | | | | | | | | | | | | |
| 305 | | | | | | | | | | | | | | | |

<210> SEQ ID NO 13
<211> LENGTH: 334
<212> TYPE: DNA
<213> ORGANISM: Aspergillus tubingensis
<220> FEATURE:
<221> NAME/KEY: Unsure
<222> LOCATION: (10)..(10)
<223> OTHER INFORMATION: Unsure
<221> NAME/KEY: CDS
<222> LOCATION: (18)..(329)

<400> SEQUENCE: 13
tacccggggn tccgatt cag ttg ttc gcg caa tgg tct gcc gca gct tat    50

```
                    Gln Leu Phe Ala Gln Trp Ser Ala Ala Ala Tyr
                     1               5                  10 tgc tcg aat aat atc gac tcg aaa gav tcc aac ttg aca tgc acg gcc        98
Cys Ser Asn Asn Ile Asp Ser Lys Xaa Ser Asn Leu Thr Cys Thr Ala
             15                  20                  25 aac gcc tgt cca tca gtc gag gag gcc agt acc acg atg ctg ctg gag       146
Asn Ala Cys Pro Ser Val Glu Glu Ala Ser Thr Thr Met Leu Leu Glu
         30                  35                  40 ttc gac ctg tat gtc act cag atc gca gac ata gag cac agc taa ttg       194
Phe Asp Leu Tyr Val Thr Gln Ile Ala Asp Ile Glu His Ser     Leu
 45                  50                  55 aac agg acg aac gac ttt tgg agg cac agc cgg ttt cct ggc cgc gga       242
Asn Arg Thr Asn Asp Phe Trp Arg His Ser Arg Phe Pro Gly Arg Gly
         60                  65                  70 caa cac caa caa gcg gct cgt ggt cgc ctt ccg ggg aag cag cac gat       290
Gln His Gln Gln Ala Ala Arg Gly Arg Leu Pro Gly Lys Gln His Asp
 75                  80                  85                  90 tga gaa ctg gat tgc taa tcy tga ctt cat cct ggr aga taacg             334
    Glu Leu Asp Cys     Xaa     Leu His Pro Xaa Arg
                         95                  100

<210> SEQ ID NO 14
<211> LENGTH: 57
<212> TYPE: PRT
<213> ORGANISM: Aspergillus tubingensis
<220> FEATURE:
<221> NAME/KEY: UNSURE
<222> LOCATION: (20)..(20)
<223> OTHER INFORMATION: UNSURE

<400> SEQUENCE: 14

Gln Leu Phe Ala Gln Trp Ser Ala Ala Ala Tyr Cys Ser Asn Asn Ile
 1               5                  10                  15

Asp Ser Lys Xaa Ser Asn Leu Thr Cys Thr Ala Asn Ala Cys Pro Ser
             20                  25                  30

Val Glu Glu Ala Ser Thr Thr Met Leu Leu Glu Phe Asp Leu Tyr Val
         35                  40                  45

Thr Gln Ile Ala Asp Ile Glu His Ser
     50                  55

<210> SEQ ID NO 15
<211> LENGTH: 33
<212> TYPE: PRT
<213> ORGANISM: Aspergillus tubingensis

<400> SEQUENCE: 15

Leu Asn Arg Thr Asn Asp Phe Trp Arg His Ser Arg Phe Pro Gly Arg
 1               5                  10                  15

Gly Gln His Gln Gln Ala Ala Arg Gly Arg Leu Pro Gly Lys Gln His
             20                  25                  30

Asp

<210> SEQ ID NO 16
<211> LENGTH: 4
<212> TYPE: PRT
<213> ORGANISM: Aspergillus tubingensis

<400> SEQUENCE: 16

Glu Leu Asp Cys
 1
```

```
<210> SEQ ID NO 17
<211> LENGTH: 5
<212> TYPE: PRT
<213> ORGANISM: Aspergillus tubingensis
<220> FEATURE:
<221> NAME/KEY: UNSURE
<222> LOCATION: (4)..(4)
<223> OTHER INFORMATION: UNSURE

<400> SEQUENCE: 17

Leu His Pro Xaa Arg
1               5

<210> SEQ ID NO 18
<211> LENGTH: 1833
<212> TYPE: DNA
<213> ORGANISM: Aspergillus tubingensis
<220> FEATURE:
<221> NAME/KEY: Unsure
<222> LOCATION: (3)..(3)
<223> OTHER INFORMATION: Unsure
<221> NAME/KEY: exon
<222> LOCATION: (372)..(453)
<221> NAME/KEY: exon
<222> LOCATION: (506)..(672)
<221> NAME/KEY: exon
<222> LOCATION: (719)..(1054)
<221> NAME/KEY: exon
<222> LOCATION: (1108)..(1413)

<400> SEQUENCE: 18
ccndttaatc ccccaccggg gttcccgctc ccggatggag atggggccaa aactggcaac      60
ccccagttgc gcaacggaac aaccgccgac ccggaacaaa ggatgcggat gaggagatac    120
ggtgcctgat tgcatggctg gcttcatctg ctatcgtgac agtgctcttt gggtgaatat    180
tgttgtctga cttaccccgc ttcttgcttt ttccccctg aggccctgat ggggaatcgc    240
ggtgggtaat atgatatggg tataaaaggg agatcggagg tgcagttgga ttgaggcagt    300
gtgtgtgtgt gcattgcaga agcccgttgg tcgcaaggtt ttggtcgcct cgattgtttg    360
tataccgcaa g atg ttc tct gga cgg ttt gga gtg ctt ttg aca gcg ctt    410
            Met Phe Ser Gly Arg Phe Gly Val Leu Leu Thr Ala Leu
              1               5                  10 gct gcg ctg ggt gct gcc gcg ccg gca ccg ctt gct gtg cgg a            453
Ala Ala Leu Gly Ala Ala Ala Pro Ala Pro Leu Ala Val Arg
   15                  20                  25 gtaggtgtgc cgatgtgag atggttggat agcactgatg aagggtgaat ag gt  gtc      510
                                                         Ser Val tcg act tcc acg ttg gat gag ttg caa ttg ttc gcg caa tgg tct gcc      558
Ser Thr Ser Thr Leu Asp Glu Leu Gln Leu Phe Ala Gln Trp Ser Ala
30                  35                  40                  45 gca gct tat tgc tcg aat aat atc gac tcg aaa gac tcc aac ttg aca      606
Ala Ala Tyr Cys Ser Asn Asn Ile Asp Ser Lys Asp Ser Asn Leu Thr
                50                  55                  60 tgc acg gcc aac gcc tgt cca tca gtc gag gag gcc agt acc acg atg      654
Cys Thr Ala Asn Ala Cys Pro Ser Val Glu Glu Ala Ser Thr Thr Met
            65                  70                  75 ctg ctg gag ttc gac ctg tatgtcactc agatcgcaga catagagcac              702
Leu Leu Glu Phe Asp Leu
            80 agctaatttg aacagg acg aac gac ttt gga ggc aca gcc ggt ttc ctg gcc    754
               Thr Asn Asp Phe Gly Gly Thr Ala Gly Phe Leu Ala
                                85                  90                  95 gcg gac aac acc aac aag cgg ctc gtg gtc gcc ttc cgg gga agc agc      802
Ala Asp Asn Thr Asn Lys Arg Leu Val Val Ala Phe Arg Gly Ser Ser
```

-continued

```
                       100                    105                    110
acg att gag aac tgg att gct aat ctt gac ttc atc ctg gaa gat aac              850
Thr Ile Glu Asn Trp Ile Ala Asn Leu Asp Phe Ile Leu Glu Asp Asn
            115                    120                    125 gac gac ctc tgc acc ggc tgc aag gtc cat act ggt ttc tgg aag gca              898
Asp Asp Leu Cys Thr Gly Cys Lys Val His Thr Gly Phe Trp Lys Ala
        130                    135                    140 tgg gag tcc gct gcc gac gaa ctg acg agc aag atc aag tct gcg atg              946
Trp Glu Ser Ala Ala Asp Glu Leu Thr Ser Lys Ile Lys Ser Ala Met
    145                    150                    155 agc acg tat tcg ggc tat acc cta tac ttc acc ggg cac agt ttg ggc              994
Ser Thr Tyr Ser Gly Tyr Thr Leu Tyr Phe Thr Gly His Ser Leu Gly
160                    165                    170                    175 ggc gca ttg gct acg ctg gga gcg aca gtt ctg cga aat gac gga tat             1042
Gly Ala Leu Ala Thr Leu Gly Ala Thr Val Leu Arg Asn Asp Gly Tyr
                180                    185                    190 agc gtt gag ctg gtgagtcctt cacaaaggtg atggagcgac aatcgggaac                  1094
Ser Val Glu Leu
            195 agacagtcaa tag tac acc tat gga tgt cct cga atc gga aac tat gcg             1143
                Tyr Thr Tyr Gly Cys Pro Arg Ile Gly Asn Tyr Ala
                                    200                    205 ctg gct gag cat atc acc agt cag gga tct ggg gcc aac ttc cgt gtt             1191
Leu Ala Glu His Ile Thr Ser Gln Gly Ser Gly Ala Asn Phe Arg Val
        210                    215                    220 aca cac ttg aac gac atc gtc ccc cgg gtg cca ccc atg gac ttt gga             1239
Thr His Leu Asn Asp Ile Val Pro Arg Val Pro Pro Met Asp Phe Gly
    225                    230                    235 ttc agt cag cca agt ccg gaa tac tgg atc acc agt ggc aat gga gcc             1287
Phe Ser Gln Pro Ser Pro Glu Tyr Trp Ile Thr Ser Gly Asn Gly Ala
240                    245                    250                    255 agt gtc acg gcg tcg gat atc gaa gtc atc gag gga atc aat tca acg             1335
Ser Val Thr Ala Ser Asp Ile Glu Val Ile Glu Gly Ile Asn Ser Thr
                260                    265                    270 gcg gga aat gca ggc gaa gca acg gtg agc gtt gtg gct cac ttg tgg             1383
Ala Gly Asn Ala Gly Glu Ala Thr Val Ser Val Val Ala His Leu Trp
            275                    280                    285 tac ttt ttt gcg att tcc gag tgc ctg cta taactagacc gactgtcaga              1433
Tyr Phe Phe Ala Ile Ser Glu Cys Leu Leu
        290                    295 ttagtggacg ggagaagtgt acataagtaa ttagtatata atcagagcaa cccagtggtg           1493
gtgatggtgg tgaaagaaga aacacattga gttcccatta cgkagcagwt aaagcacktk           1553
kggaggcgct ggttcctcca cttggcagtt ggcggccatc aatcatcttt cctctccta            1613 ctttcgtcca ccacaactcc catcctgcca gctgtcgcat ccccgggttg caacaactat           1673
cgcctccggg gcctccgtgg ttctcctata ttattccatc cgacggccga cgtttcaccc           1733
tcaacctgcg ccgccgcaaa atctccccga gtcggtcaac tccctcgaac cgccgcccgc           1793
atcgacctca cgaccccgac cgtctgygat ygtccaaccg                                 1833
```